US010706129B2

(12) United States Patent
Konoske et al.

(10) Patent No.: US 10,706,129 B2
(45) Date of Patent: Jul. 7, 2020

(54) MEDICAL LOGISTICS MANAGEMENT PROGRAM

(71) Applicants: Paula Konoske, San Diego, CA (US); Michael Galarneau, San Diego, CA (US); Ray Mitchell, Huntsville, AL (US); Johnny Brock, Brownsboro, AL (US)

(72) Inventors: Paula Konoske, San Diego, CA (US); Michael Galarneau, San Diego, CA (US); Ray Mitchell, Huntsville, AL (US); Johnny Brock, Brownsboro, AL (US)

(73) Assignee: The United States of America as represented by the Secretary of the Navy, Arlington, VA (US)

( * ) Notice: Subject to any disclaimer, the term of this patent is extended or adjusted under 35 U.S.C. 154(b) by 379 days.

(21) Appl. No.: 14/192,521

(22) Filed: Feb. 27, 2014

(65) Prior Publication Data

US 2015/0242577 A1    Aug. 27, 2015

(51) Int. Cl.
*G06F 19/00* (2018.01)
*G16H 40/20* (2018.01)
(Continued)

(52) U.S. Cl.
CPC ......... *G06F 19/3481* (2013.01); *G16H 40/20* (2018.01); *G16H 50/50* (2018.01); *G16H 50/30* (2018.01)

(58) Field of Classification Search
CPC ............ G06F 19/322; G06F 17/30876; G06F 3/0482; G06F 3/04842; G16H 10/60
See application file for complete search history.

(56) References Cited

U.S. PATENT DOCUMENTS

2013/0066609 A1*   3/2013   Gilkes ............... G06F 17/30241
                                                              703/6

OTHER PUBLICATIONS

TML+V. 2.0 (Konoske et. Al; TML+ Tactical Medical Logistics Planning Tool Version 2.0 User's Guide; Report date: Mar. 11, 2004).*

(Continued)

*Primary Examiner* — Linh Giang Le
(74) *Attorney, Agent, or Firm* — Ning Yang; Albert Churilla; Diane Tso

(57) ABSTRACT

This invention are computer implementable programs and method designed as medical planning tool that (1) models the patient flow from the point of injury through more definitive care, and (2) supports operations research and systems analysis studies, operational risk assessment, and field medical services planning. The computer program of this invention comprises six individual modules, including the casualty generation module, which uses an exponential distribution to stochastically generate wounded in action, disease, and nonbattle injuries; a care providing module uses generic task sequences, simulated treatment times, and personnel, consumable supply, and equipment requirements to model patient treatment and queuing within a functional area; a network/transportation module simulates the evacuation (including queuing) and routing of patients through the network of care via transportation assets; a reporting module produces an database detailing various metrics, such as patient disposition, time-in-system data, and consumable, equipment, personnel, and transportation utilization rates, which can be filtered according to the user's needs.

7 Claims, 19 Drawing Sheets

Block diagrams indicate top-level decision tree for a operational scenario

(51) Int. Cl.
    G16H 50/50    (2018.01)
    G16H 50/30    (2018.01)

(56) References Cited

OTHER PUBLICATIONS

Tropeano, Konoske, Galarneau, Mitchell, Brock, Parker, The Development of the Tactical Medical Logistics Planning Tool (TML+), Tropeano, A. and P. Konoske. 2002. Estimating Supplies Program Version 2.00: User's Guide. NHRC Tech. Doc. No. 02-1A. Naval Health Research Center, San Diego, CA.

Konoske, Galarneau, Pang, Brock, Lowe, Mitchell, Parker, Daly, Choi, Edwards, Hill, Tropeano, TML+ Tactical Medical Logistics Planning Tool Version 2.0 User's Guide, Naval Health Research Center P.O. Box 85122 San Diego, CA 92186-5122, www.nhrc.navy.mil/tml.

Mitchell, Galarneau, Hancock, Lowe, Modeling Dynamic Casualty Mortality Curves in the Tactical Medical Logistics (TML+) Planning Tool, Technical Report No. 04-31, conducted under Work Unit 63706N M0095.005-60320.

Mitchell, Onofrio, Konoske, Brock, Parker, Ship to Objective Maneuver: Medical Analysis Using the NHRC Tactical Medical Logistics Planning Tool in Support of the Marine Corps Wartighting Lab, Report No. 05-33 under Work Unit No. 63706N-M0095-60315.

Konoske, Galarneau, Pang, Adlich, Brock, Lowe, Mitchell, Parker, Daly, Hill, Onofrio, TML+ Tactical Medical Logistics Planning Tool User's Manual Version 4.1, Mar. 9, 2006, Naval Health Research Center P.O. Box 85122 San Diego, CA 92186-5122, www.nhrc.navy.mil/programs/tml.

Brock, Adlich, Onofrio, Konoske, Operations in Complex and Distributed Environments: A Case Study Using the Tactical Medical Logistics Planning Tool (TML+), Technical Document No. 07-31, Naval Health Research Center, P.O. Box 85122, Sand Diego, California 92186-5122.

Onofrio, Brock, Adlich, Konoske, Using TML+ to Validate the Expeditionary Resuscitative Surgical System, Technical Document No. 07-30 under Work Unit 63706N M0095.005-60512, Naval Health Research Center, P.O. Box 35122, San Diego, California, 92186-5122.

Konoske, Adlich, Medical Battalion Enhancement Initiative: Impact of Surgical Assist Teams, Presentation given at the 78th Military Operations Research Society Symposium (MORSS) held Jun. 22-24, 2010 at the Marine Corps Combat Development Command (MCCDC) in Quantico, VA.

Davis, Mitchell, Konoske, Tactical Medical Logistics (TML+) Planning Tool: A Crisis Action Planning Module, Technical Document No. 099-1A under Work Unit No. 63706NM0095.005-60315.

Mitchell, Parker, Galarneau, Konoske, Combat Mortality Using the Navy-Marine Corps Combat Trauma Registry Expeditionary Medical Encounter Database for Applications to Tactical Medical Logistics Modeling and Simulation, Naval Health Research Center Document No. 09-33, Naval Health Research Center, 140 Sylvester Rd., San Diego, California 92106-3521.

Adlich, Brown, Wing, LHA(R) Medical Space Configuration Study for Sea Base Sustainment of Operations, presentation given Jun. 20, 2011 at the 79th Military Operations Research Society Symposium, Monterey, California.

Mitchell, Brown, Konoske, Brock, Galarneau, Parker, Modeling, Simulation, and Analysis of Tactical LMedical Logistics Systems: Ten Years of Successes at the Naval Health Research Center and New Initiatives, Presentation given Jun. 13, 2012 at the 80th Military Operations Research Symposium held at the Air Force Academy in Colorado Springs, Colorado.

Galarneau, Pang, Konoske, Projecting Medical Supply Requirements for a Highly Mobile Forward Resuscitative Surgery System, Report No. 99-29 under Work Unit No. 63706N-M0095-6809, Naval Health Research Center, Medical Information Systems and Operations Research Department, P.O. Box 85122, San Diego, California, 92186-5122.

Mitchell, Parker, Galarneau, Konoske, Statistical Modeling of Combat Mortality Events by Using Subject Matter Expert Opinions and Operation Iraqi Freedom Empirical Results from the Navy-Marine Corps Combat Trauma Registry, Journal of Defense Modeling and Simulation: Applications, Methodology, Technology, XX(X) 1-11, 2010 The Society for Modeling and Simulation International DOI: 10.1177/1548512910364755.

Mitchell, Galarneau, Hancock, Lowe, Modeling Dynamic Casualty Mortality Curves in the Tactical Medical Logistics (TML+) Planning Tool, Report No. 04-31 conducted under Work Unit 63076N M0095.005-60320, Naval Health Research Center, P.O. Box 85122, San Diego, California, 92186-5122.

Hill, Galarneau, Konoske, Pang, Marine Corps Operational Medicine: Determining Medical Supply Needs of the Forward Resuscitative Surgery, Technical Report No. 05-30 under work unit 63706N M0095.005-60120, Naval Health Research Center, P.O. Box 85122, San Diego, California, 92186-5122.

Galarneay, Konoske, Emens-Hesslink, Pang, Reducing the Logistical Footprint of Forward Resuscitative Surgical Units Using a Patient-Driven Model of Clinical Events, Naval Health Research Center, Medical Information Systems and Operation Research Department, P.O. Box 85122, San Diego, California, 92186-5122.

* cited by examiner

Figure 3

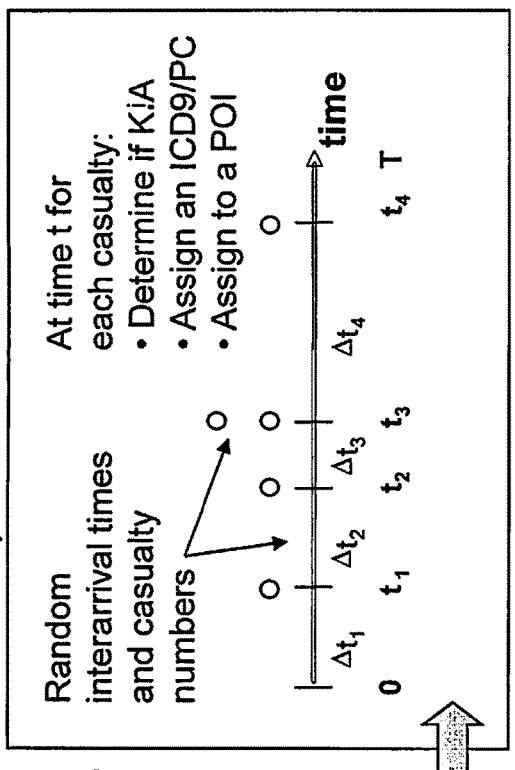

Simulation Modeling (for scenario duration or for user defined blocks of time within)

Top-level steps:

1. Loop for each PSG (User enters PSG Type... Single Rate, Multiple Rate Table, Mass Casualty Event along with PCOF, Type of Casualty (WIA, DIS, NBI, CS), and POI/probabilities)
   a. For each PSG type, generate set of event times $t_1, t_2, \ldots$ with exponential interarrival times, $\Delta t$
   b. For each time designated for a MCE, generate number of casualties with geometric $(1, 2, \ldots)$
   c. For each WIA casualty determine if KIA or not (a Bernoulli trial -- ie, a coin toss (0,1) from KIA/WIA rate)
      (1) If KIA, log as death for Reports module
      (2) If not KIA, randomly sample from input PC distribution for ICD9/PC
   d. For ICD9/PC, randomly assign to a POI from user input distribution
   e. For each ICD9/PC associate data from commondata.sdf
   Repeat above for each replication $1, 2, \ldots, n$
2. After all looping is complete, go to Care Providing Module for 1st MTF in N/T module (ie, have n sets of patient streams for subsequent use in remainder of modules)

Figure 6
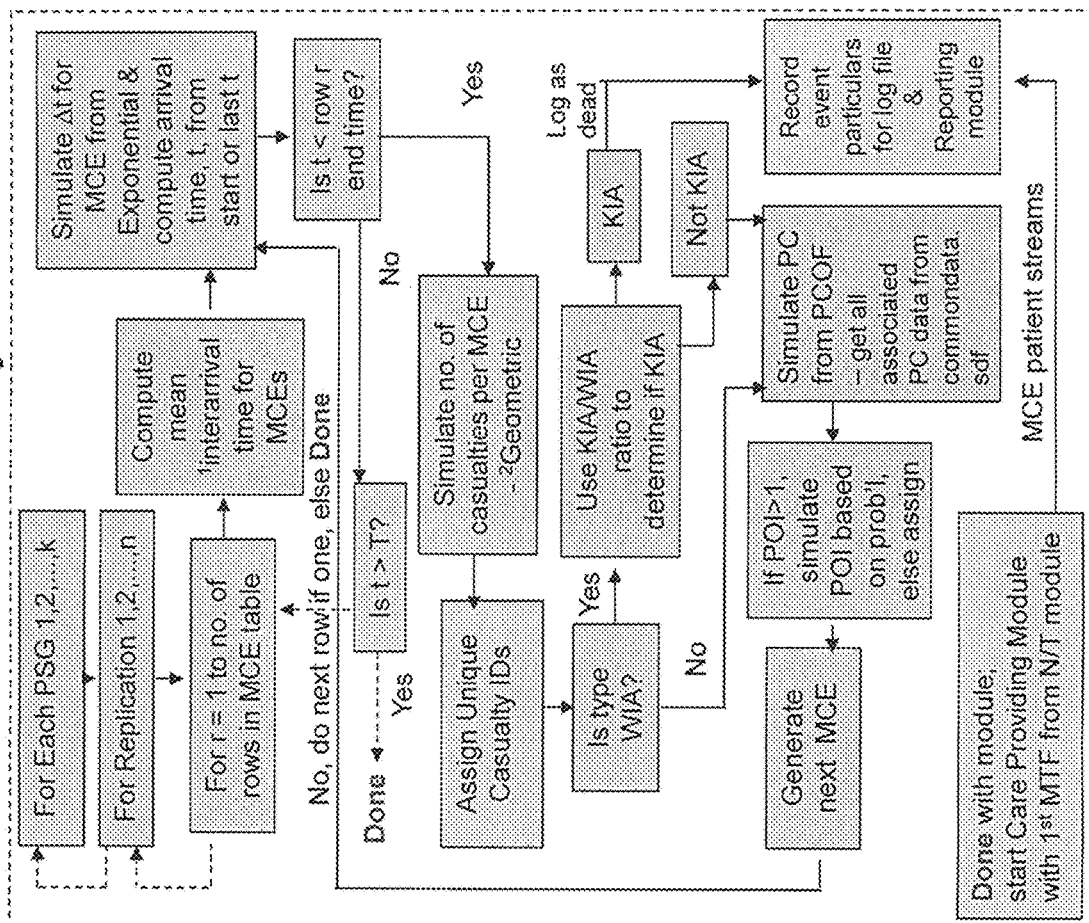
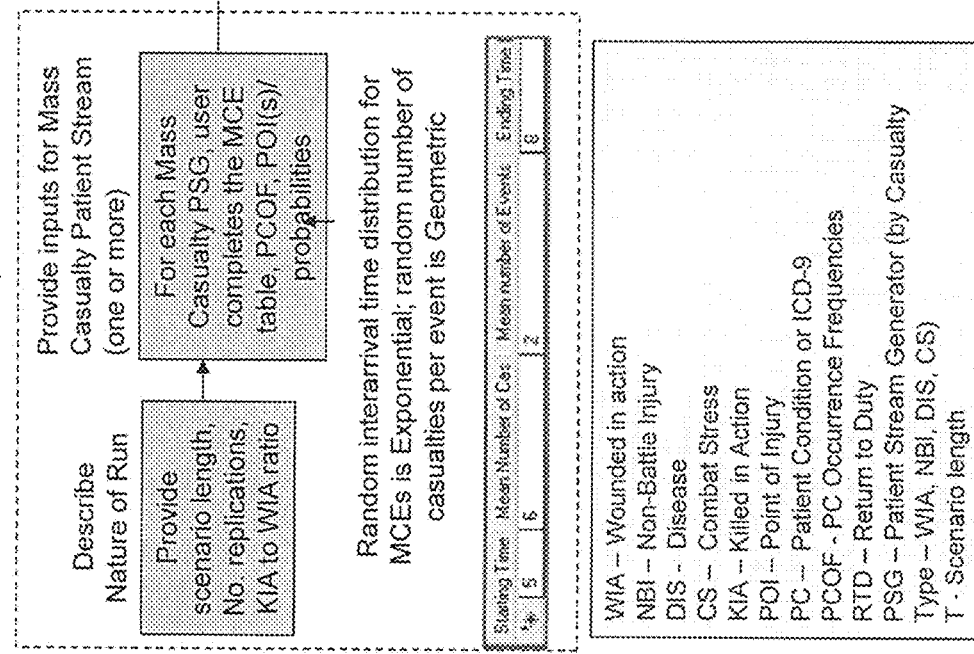

Figure 12
Top-Level View of DOW Algorithm

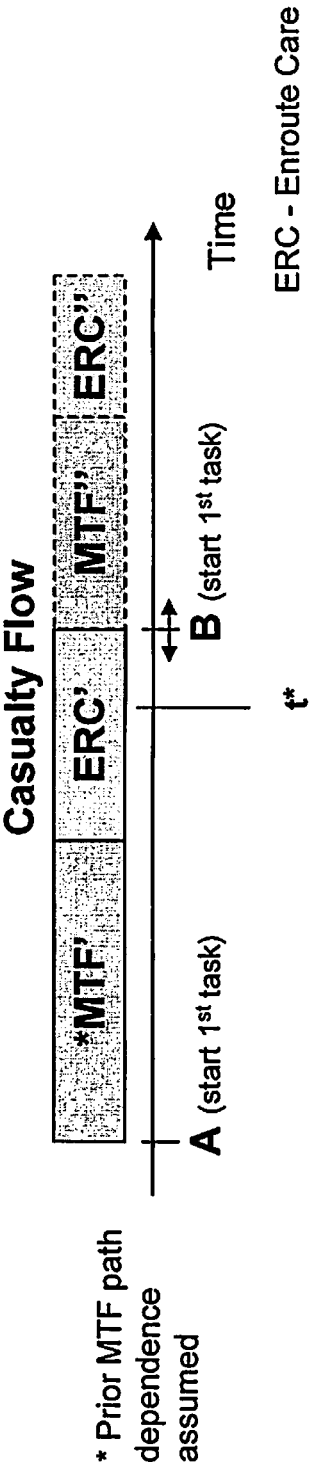

Method: A death time, $t^*$, through MTF' & ERC' is simulated at A (by inverting F(t) with Weibull coefficients {a,b} conditional on patient condition, path history and MTF')

- If $t^* <= B-A = \theta$, then the casualty dies at $t^*$ and is removed from the simulation; all resources are freed up (during a task or in queueing for a task waiting to be started)

- If $t^* > \theta$, then the casualty survives this MTF' and ERC' and starts over with a new $t^*$ from an improved F(t) in the next facility, MTF'' (an assumed growth in survivability model)

Note: $\theta$ will vary as B varies depending on treatment and evacuation timing driven by resource constraints and operating rules. The subsequent decision point ($t^*$ vs $\theta$) provides a rich trade space for sensitivity analyses of mortality impacts in resolving most medical planning issues.

MEDICAL LOGISTICS MANAGEMENT PROGRAM

STATEMENT REGARDING FEDERALLY SPONSORED RESEARCH OR DEVELOPMENT

This invention was made with Government support under contracts (W911QY-08-D-0018 and W911QY-08-D-0058) awarded by USARDEC (United States Army Research, Development and Engineering Command. The Government has certain rights in the invention.

CROSS-REFERENCE TO RELATED APPLICATION

This application claims priority to U.S. Provisional Application No. 61/769,805, filed Feb. 27, 2013.

FIELD OF THE INVENTION

The present invention relates in general to a computer tool used in medical logistics planning and modeling. More particularly, this invention relates to computer implemented programs, and method for building and evaluating medical logistic plans for an operational scenario, whether it is a military maneuver or a rescue response. This invention is capable of modeling casualty and mortality associated with an operational scenario using a pre-determined medical logistic plan, and can be used to evaluate the medical resources required for the operation. The mortality in particular may be modeled as killed in action, died of wounds as a function of complications, and died of wounds as a function of time. The inventive computer program can also be used to assess adequacy of different medical logistic plans based simulations of a broad range of stochastic events associated with a casualty's disposition from the point of injury (POI) to definitive care.

DESCRIPTION OF THE RELATED ART

In conventional military and crisis response operations, difficulty is frequently encountered in estimating casualties and mortalities associated with the operation, and medical resources required for an operational scenario, which impact the accurate planning of a forward resuscitative surgical system (FRSS) in the field. A FRSS provides emergency surgical interventions to stabilize casualties who might otherwise die or lose limbs before reaching a traditional treatment facility. Because it is forward located, casualties will get to the FRSS fast and once there, the right medical staff will be available to treat them. Under a FRSS, the equipment being unpacked and installed will provide exactly what the medical personnel need, without the burden of unnecessary items, which require additional storage space, transportation and costs. Under FRSS, within hours, a full-functioning medical treatment facility will be available to provide life-saving care, and transportation will be available to quickly move casualties in and out. This invention allows different levels of medical treatment facilities and their locations and all associated assets to be carefully planned through virtual means, without risking actual lives, and for far less cost than conducting live exercises and war games.

Before the development of this invention, the "stubby pencil" and "back of the envelope" approaches that relied heavily on anecdotal evidence and subject matter expertise were the primary tools available for operational planning by military and civilian medical planners. Some useful, but not comprehensive medical modeling and simulation tools were used in an attempt to virtually determine the minimum capability necessary to maximize medical outcomes, and ensure success of the FRSS plan, including Ground casualty projection system (FORECAS) and the Medical Analysis Tool (MAT).

FORECAS produced casualty streams by day of the conflict but neither specified the type of injury nor the injury time. MAT and later the Joint Medical Analysis Tool (JMAT) consist of two modules. One module is designed as a requirements estimator for the joint medical treatment environment while the other nodule is a course of action assessment tool. Medical planners use MAT to generate medical requirements needed to support patient treatment within a joint warfighting operation. MAT estimated the number of beds, the number of operating room tables, number and type of personnel, and the amount of blood required for casualty streams, but was focused at the Theater Hospitalization level of care. Furthermore, MAT treated the theater medical capabilities as consisting of three levels of care, but did not take into account of medical treatment facilities (MTFs) at each level, their spatial arrangements on a battlefield, nor the transportation assets necessary to interconnect the network. MAT was a DOD-owned software program that did not include a Marine Corps model, and was designed as a high-level planning tool for Echelon 3 organization (Theater Hospitalization). MAT did not include the capability to evaluate forward medical capabilities such as the FRSS, nor did it provide a realistic evaluation of mortality. JMAT (the MAT successor) failed Verification and Validation testing in August 2011, and the program was cancelled by the Force Health Protection Integration Council. Other simulations were described by Von Tersch et al. [1].

These existing methods or software provide useful information for preparing for a mission. However, there is still the need to model the flow of casualties within a specific network of treatment facilities from the generation of casualties through the treatment system, simulating the treatment times, and demands on consumable supplies, equipment, personnel, and transportation assets in the far-forward environment.

DETAILED DESCRIPTION OF DRAWINGS

FIG. 1 General Diagram illustrating a simplified medical logistic plan based on an operational scenario using the present invention.

FIG. 2 An exemplary map illustrating a medical logistic plan selected for an operational scenario.

FIG. 3 A Top-Level View of the Casualty Generation Module.

FIG. 4 A block diagram illustrating the flow of data in single rate Patient Stream Generator of the Casualty Generation Module.

FIG. 5 A block diagram illustrating the flow of data in multiple rate Patient Stream Generator of the Casualty Generation Module.

FIG. 6 A block diagram illustrating the flow of data in mass casualty event Patient Stream Generator of the Casualty Generation Module.

FIG. 7 Care Providing Module Top-Level Flow & Basic Algorithm of the Care Providing Module FIG. 8 Illustrating the MTF Network Flow Involving New and Customers within Functional Area FIG. 9 Casualty Flow within the MTF—Algorithm Overview FIG. 10 Care Providing Module Flow Chart 1

FIG. 11 Care Providing Module Flow Chart 2

FIG. 12 Shows a Top-Level View of DOW Algorithm

DETAILED DESCRIPTION OF THE INVENTION

Definition of Terms Used Herein

Figure 1:
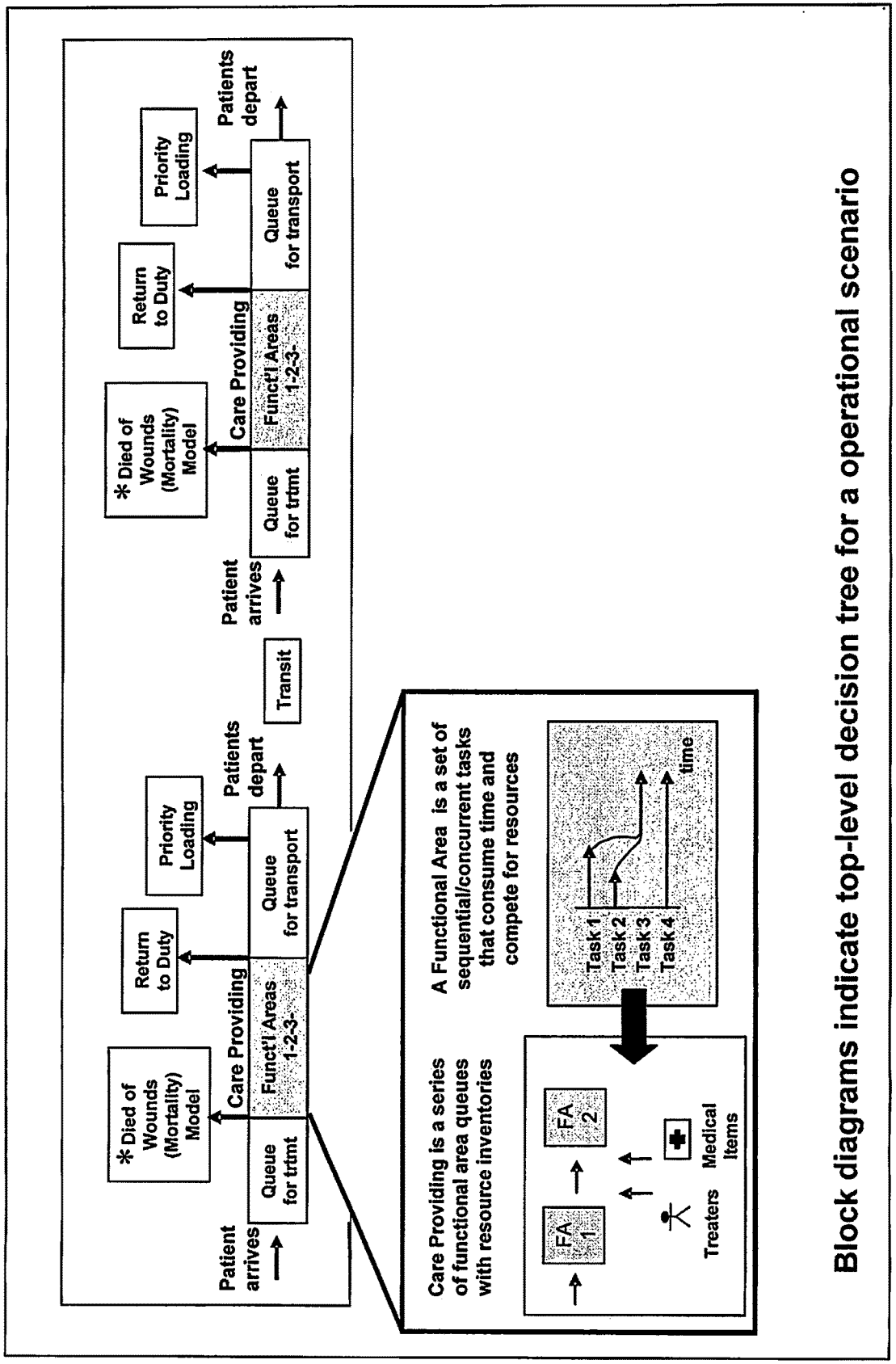

Database is a collection of Tables and Views with associated stored procedures.

Entity is a person, thing, or abstract business concept. In database design, entity is the thing that the Table represents.

Field is a single column of information in a Table.

Foreign Key is a Primary Key from one table that is in another table to establish a relationship between the two tables.

Primary Key is a unique identifying value in a record of a table.

Record is a single row of information in a table.

Scenario is a situation that results in a patient stream. Also, often used as a synonym of patient stream.

Stored Procedure is code within a database used to maintain tables, assign key values.

Supply is a piece of equipment, durable item, or consumable item that is used in the treatment of patients.

Table is information about a particular entity stored in a series of records with the same fields.

Task is a medical procedure performed on a patient.

View is the updateable result of a query. Several views are stored in the database.

A parameterized view requires parameters that are used in running the query to produce the result.

A AMAL (Authorized Medical Allowance List) is a collection of medical supplies grouped for use by functional area.

BAS Battalion Aid Station is a far-forward medical treatment facility (MTF) that offers clinical assessment; treatment administered includes use of intravenous fluids and antibiotics, reservation of the airway by surgical procedure, and application of more secure splints and/or bandages. The BAS provides initial resuscitation and routine health services and carries the theater sick-call supplies.

Capabilities-based sets are medical supplies grouped by their function and usage within a treatment facility.

CASEVAC Casualty evacuation system is the evacuation system that renders care during patient transport from the point of injury (POI) to a collection point or MTF.

Casualty Generators generates a stream of casualties/patients that arrives at a randomly generated time and location with randomly generated patient conditions. In this invention, the various methods used to calculate casualty numbers include by rate, by table, or by user-defined rates.

Colocated Medical Treatment Facility are MTFs grouped together to augment the medical services they provide. For instance, an FRSS and an STP may be placed together to add operating room tables and hence the ability to perform life- and limb-saving procedures.

Common Database is an object within a scenario that represents the medical capability and transportation types that may be reused. The Common Database also incorporates data for over 400 patient conditions and the corresponding medical treatment tasks.

CRTS Casualty Receiving Treatment Ship is a general-purpose amphibious assault ship that receives, provides treatment for, and transfers casualties. Its objectives are to save life and limb, provide initial resuscitative treatment, and perform stabilization for evacuation of casualties whose medical requirements exceed its capabilities. CRTS capabilities include triage, lab, x-ray, operating room (OR), ward, pharmacy, dental, battle dressing station, portable medical locker, antidote locker, first-aid box, emergency response kit (ERK), junior ERK, and preventive medicine (PM) capability. CRTS is modeled with the medical capabilities, personnel, and supplies of a Surgical Company (SC).

DIS (Disease) is a casualty type designation indicating that the person presented at an MTF with an illness.

DOW stands for Dead of wounds or died of wounds.

ERCS (En Route Care System) is medical capability that provides treatment while in transit. ERCS has three phases: casualty evacuation (CASEVAC), tactical medical evacuation (MEDEVAC), and strategic evacuation. (See each of those entries for more specific definitions.)

FA (Functional Area) is a medical capability within an MTF designated for a specific purpose (e.g., the OR, or the x-ray component).

FRSS Forward Resuscitative Surgical System—A medical capability that provides limited triage/preoperative trauma management and postoperative holding capability, and is equipped to provide life- and limb-saving surgical procedures. Includes triage, OR, and ward (with limited holding capability). An FRSS can serve as a forward element of the SC or as a stand-alone surgical element colocated with a BAS or STP.

Iteration(s) is also called a run, it is the number of times a scenario is "run", or simulated.

KIA (Killed in action) are casualties who die on the battlefield or those who do not receive any medical care.

MEDEVAC (Medical evacuation system) is the evacuation system that provides care during evacuation from a BAS, STP, FRSS, or SC to a theater hospital.

MTF (Medical treatment facility) is any of a number of different configurations of medical materials and personnel combined to provide various levels of medical care.

NBI (Nonbattle injury) are injury incurred while engaged in any activity performed outside the battlefield.

Objects are the parts of invention computer program and its scenario-building functions that include casualty generators, points of injury, medical capabilities, MTFs, transportation assets, and routes between MTFs.

OR (Operating Room) is a functional area within an MTF. The OR provides resuscitative/stabilizing surgery to casualties unlikely to survive MEDEVAC.

Patient queuing is the part of inventive computer program drawing a population of casualties through a medical treatment network that dictates the order in which patients will be treated.

Patient stream is a list of patient conditions and the associated number of patients exhibiting that condition. It describes the specific configuration of casualties (in PC Code descriptors) that a scenario may include, in some cases stochastically calculated, based on probabilities established by the casualty estimation tools such as FORECAS and/or CASEST.

PC or PC Code stands for Patient Condition code, which is three-digit number describing casualty patients' injuries, physical conditions, or diseases. A group of 400 or so PCs were formulated by the Defense Medical Standardization Board to standardize diagnostic formats across medical resource models. PC codes constitute the underlying data on which this invention and other medical modeling and simulation programs draw.

POI Point of injury indicates a geographical site on the battlefield where injury occurs In this invention, it is considered the point from which the First Responder must move or transport the injured individual.

Properties are details of those variables that define objects within a scenario. For instance, to establish overall units of measure for time or distance, the user navigates within the Properties box to select either days or hours (for time), or kilometers (km), miles (mi), or nautical miles (nm) (for distance). Properties may also determine scenario parameters such as mean number or type of casualty, or types of behavior within an evacuation route for an MTF.

Random Seed Number: as a stochastic model, this invention uses random draws to simulate a scenario. This process requires a random seed number, used to initialize the random number generator. A large prime number works best. Replications Each replication represents a patient stream being run through a simulated treatment network once. The user may define the number of times the stream is put through the simulation so as to get a representative sample.

Runs are the number of times a given scenario is run. See also Iteration.

SBA (Self-Buddy Aid) is the treatment at the POI that each patient gives themselves or receives from another troop.

SC (Surgical Company) is an MTF that typically has greater surgical and medical capabilities than a BAS, including triage, OR, ward, x-ray, laboratory, pharmacy, dental, and preventive medicine functional areas. SC objectives are to save life and limb, provide initial resuscitative treatment, and perform stabilization for evacuating casualties whose medical requirements exceed SC capabilities.

Service discipline refers to the two rules by which a patient stream is queued: either based on a first-in, first-out basis (FIFO) or one which dictates that the casualty with the worst injuries is treated first.

STP (Shock Trauma Platoon) is a MTF that can serve as a beach evacuation station, reinforce a BAS, operate as an intermediary casualty collecting and clearing point between forward elements and the Surgical Company (SC), or serve as the forward element of an SC (i.e., triage/evacuation platoon) preparing to relocate. STP has triage and limited operating room (OR) and ward capabilities.

Triage/SST is a functional area within an MTF that provides receipt, resuscitation, and sorting of casualties, treating casualties with battle injuries, nonbattle injuries (NBIs), and those who can return to duty within 72 hours. The triage/SST renders general surgical support and preoperative clinical functions.

Ward is a functional area within an MTF. Surgical Company ward provides monitoring and recuperative care to postoperative patients and those who can return to duty within 72 hours. FRSS ward has limited holding capabilities.

WIA is Wounded in action

X-ray is functional area within an MTF that provides x-ray and processing capabilities.

This invention aims to resolve the problems of existing modeling tools. It stochastically generates the patient stream, randomly determines time of injury, and specifies the exact injury or disease for each patient. Thus, overcoming disadvantages of FORECAS. This invention also gives specific representation of the capabilities of service-specific medical treatment facilities (MTFs), including their table of organization and table of equipment. Further, it provides the capability to position those MTFs spatially, and therefore captures the distance and routing necessary to transport patients within the theater medical network overcoming the limitations of MAT. Because of its stochastic design, the inventive program permits advanced analysis capabilities utilizing statistical methods to determine expected value results as well as percentiles, minima, maxima, etc. thus permitting risk assessment in a course of action context.

In additional to military operational use, the present invention can also be used in creating simulations of crisis response planning whether it is a natural disaster or an infectious disease break out. With historical data of similar natural disasters or public health events, the invention can be adapted as a tool used for quick planning of timely response to such crisis. In summary, this invention can be used as tool to better quantify the optimal mix of health-care facilities and providers, medical equipment and supplies, and transportation assets affecting medical delivery.

The present invention uses discrete event Monte Carlo software designed for medical planners to estimate medical resource requirements, which also permits operational risk assessments. The present invention can perform overall medical system analysis, and operation research studies for a variety of scenarios, such as military operation or natural disaster response. As a simulation tool, it models the flow of casualties from the point of wounding to definitive care. A unique feature of this invention is its capability to model mortality as a function of time before treatment. The present invention supports analysis of casualty and mortality relative to time, the location on the battlefield, and the capabilities of medical and evacuation assets.

Users enter various parameters, relating to personnel resources, number of treatment sites, treatment capability, distribution of casualties and arrival rate, and vehicle quantity, speed, and home locations. Using these inputs, the inventive software employs stochastic processes to model patient treatment and outcomes. A stochastic process is a statistical method used in this invention to create random patient stream and flow, which means that when creating a patient stream, the model takes a stochastic or random draw from the pool of underlying data that relies on assigned probabilities to determine if a particular patient condition will show up for treatment in the patient stream. For example, given the same condition, a deterministic equation would read: if this condition is present, that always occurs. However, in this invention, for example, if the first MTF is busy, then the patient moves to the next level of care.

The inventive software traces how patients proceed through treatment by stochastically generating when patients arrive into the network, how long patients wait for treatment, and how long treatment and evacuation take. The inventive software can produce dynamic reports that detail patient disposition, casualty flow and accumulation, consumable quantities, personnel and equipment utilization, and transportation usage. The inventive software can also provide a graphic representation of the assets used the location of these assets, the number of patients treated at each treatment facility, and how often the patients use them.

The present invention is also an operations research tool that supports medical decision-making, and field medical services planning. By running different sets of the aforementioned parameters for the same operational scenario, medical planners can analyze how a relocation of assets or changes to number/level/capability of MTF would affect patient treatment/outcome. Users thus can decide on the type and number of facilities mostly suitable for the mission. Users can also prioritize the needs of the mission, assess operational risk, and determine the best course of action for the anticipated patient stream with the available or projected assets, including
  (i) the quantity of supply, personnel, and transportation assets utilized by the expected patient stream;
  (ii) whether one network of facilities is more efficient than another network of facilities; and
  (iii) how relocation of a treatment facility and/or the increase or decrease in evacuation assets affects patient outcomes.

The inventive system comprises in general: a software or computer programs, at least one computing device, which is capable of controlling said computer programs, is communicative with one or more databases, wherein at least one said database stores operational statistics of historical missions. In an embodiment of this invention, the software comprises six individual modules, including: the casualty generation module, the care providing module, the networks and transportation module, the died-of-wounds module, the report generation module, and the access to database module. Each module may communicate data of the other modules to form a system incorporating data sharing, thus achieving an evaluation of emergency medical care plans or simulations of best planning strategies in a given operational scenario whether it is a military operation or a crisis response action.

FIG. 1 shows an example of the top-level decision diagram for running a scenario simulation. A patient stream start at the point of injury (POI), and the number and frequency of patient stream is created using casualty generation module in communication of the database. The number of the patients, the Patient Condition and the percentage of different Patient Conditions (PC) were estimated based on historical data of similar operations. A patent condition is an injury or disease that corresponds to a patient condition code number, and is exhibited by the patient. Patients arrive at a treatment facility with a predetermined level of care (LOC), such as self/buddy aid (SBA), a shock trauma platoon (STP), or a surgical company (SC), etc. These medical treatment facilities provide different levels of medical care, with each facility associated with a set of predetermined medical resources, including but not limited to consumable medical supplies, reusable equipment and personnel and space occupancy. The set of medical resources can be set by the user or based on the program default. Each patient is queued for treatment, which is simulated via the care providing module. For example, a medical facility may comprise of a series of functional areas with different medical resource and inventories, such availability of operation room, personnel, equipment, medication and blood supplies. During a simulation, a set of sequential and/or concurrent tasks are to run at each functional area, with patients consume time and compete for resources. A task is a medical procedure performed on a patient. The mortality rate upon arrival of the treatment facility or within care providing module/transportation module may be estimated using the died-of-wounds module. After a patient stream move through a medical treatment facility, a percent of patient stream may die from complications, recover and return to duty station, or get transported to the next level of care. The transportation available to the patients is determined by user, and simulated using the transportation module. Within the transportation module, each patient is placed, prioritized and routed, based on patient condition (PC), planned transportation capacity, and the location and availability of the next level care, service discipline and operational rules. Mortality rate during transportation may be estimated using the died-of-wounds module or simply set using the mortality rate of the previous medical treatment facility. A patient stream pass through different treatment facilities based on the simulated operational scenario, and medical logistic plan until all patients either died of wounds or recover and return to duty. The medical logistic plan and result of each simulation for that medical logistic plan may be reported and display in the desired formats.

Figure 2:
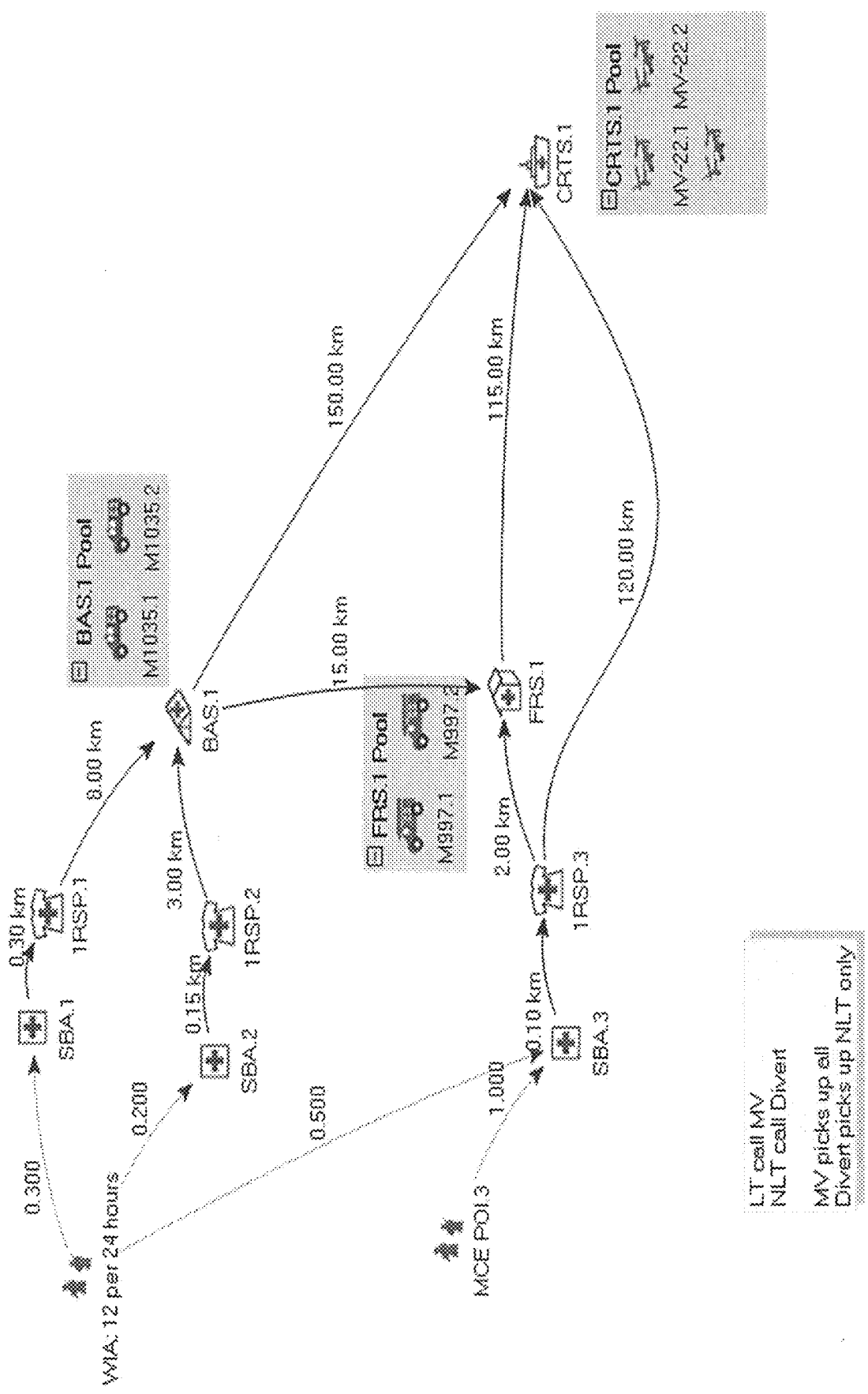

FIG. 2 is an example graphic display of a medical logistic plan for an operational scenario. All medical treatment facilities are shown on a map of the battlefield, with their locations and level of care graphically indicated. Distances between different types of medical treatment facilities (MTF) and the available transportation capability are also shown graphically. Transportation rules may also be displayed on this map.

Casualty Generation Module

FIGS. 3-6 illustrate the operation flow diagram of the casualty generation module. The casualty generation module contains a set of functions that describes casualty steams from an operational scenario. It generates a steady patient/casualty stream due to arrive at the first level medical treatment facility. Before each simulation, the user may select one of three casualty generator within the casualty generation module, including the single rate patient stream generator, the multiple table patient stream generator and the mass casualty event patient stream generator. Each casualty generator has its own decision points, which result in the generation of different patient streams. With each patient of a patient streams randomly created at different times (t) and each patient's information assigned/recorded. The user may also define the properties of the selected patient stream generator (PSG), including patient casualty occurrence frequencies (PCOF), arrival time, the type of casualty, and POI and its probabilities. PCOF is the frequency at which a particular patient condition (i.e. an injury) may occur. PCOF is a table based on historical data of similar operation scenarios, within which patient condition is identified using ICD-9 code. The types of casualty supported by the casualty generation module include wounded-in-action (WIA), disease (DIS), non-battle injury (NBI) and combat stress (CS). Point-of-injury (POI) is a geographical site on the battlefield where a casualty occurs. The inventive system supports unlimited number of POIs. Each POI has a probability associated with it that determines the percentage of the casualties that may occur at the location. Probabilities of all POI must total to 1.

Upper left box of FIG. 3 shows a comparison of input tables for the three generators. If a single rate generator is selected for casualty generation, the casualty rate entered by the user is repeated until the end of the scenario simulation. FIG. 3, User Input Box shows example of inputs used to define a single rate generator. In this single rate input box, the user entered a wounded in action rate of 10 casualties every 24 hours for the operational scenario duration. This means the casualty generation event is repeated every 24 hours at a mean rate of 10 casualties per event until the end of the scenario simulation. The user may select a multiple rates PSG if the user wants to model a pulse or pause in the patient stream. In a multiple rates casualty generator input box, the user needs to define the number and type of casualties for each blocks of time within the scenario simulation duration. As in single rate casualty generation, each time block is assigned by the user to generate only one type of injuries (WIA, DIS, NBI or CS). However, unlike in the single rate generator, the numbers of casualties that a user enterers for each casualty type is generated only once and not repeated. Therefore, the user must define a casualty rate for each time block of the simulated scenario duration. An example of multiple rate input table is shown below the single rate table in the User Inputs Box of FIG. 3. In this table, the user entered 10 casualties for the first 12 hours, and 20 for the next block of time up to 36 hours. This means that approximately 10 casualties are stochastically generated for the first 12 hour and 20 patients for hours 12 through 36. The user may also use a mass casualty events (MCEs) for the operational scenario, which is defined by the starting time, mean number of casualties, mean number of events and ending time. For example, as shown in mass casualty event input table in FIG. 3, the user inputs allows a simulation of an average of two mass casualty events to occur between the $5^{th}$ hour and the $8^{th}$ hour of the operation scenario with an average of six casualties for each event.

Once the user set up the casualty generation module, a casualty generation simulation may run with the program loop through patient stream generator (PSG during the scenario simulation duration (T). For each PSG type, casualty events occurs at times $t_1, t_2$ . . . etc., which is set with exponential interarrival times ($\Delta t$). During the time block designated for a MCE, a stochastic number of casualties are generated with the geometric distribution where the user inputs the mean number of casualties desired for their scenario.

For each WIA casualty generated, a killed in action (KIA) determination must be made. KIA refers to troops who die on the battlefield at the time of injury and receive no medical care. KIA is entered as a ratio by the user before each simulation. The numerator of KIA is the number of troops expected to be killed. The denominator of KIA is the number of wounded in action (WIA). For example, if the KIA ratio is 1 to 100 and the scenario has 500 WIAs, approximately 5 troops will be stochastically generated as KIA according to a Bernoulli trial (coin toss). If a casualty generated and not assigned as KIA, a patient condition (PC) is assigned to the casualty using ICD-9 code. The patient condition assignments are randomly sampled from a PC distribution, which is decided by the user via PSG input. For each PC, its associated data such as treatment required, can be found and imported from database commondata.sdf. The casualty generation loop is repeated. After simulation is complete, the program proceeds to Care Providing Module for $1^{st}$ MTF in network.

Figure 4:
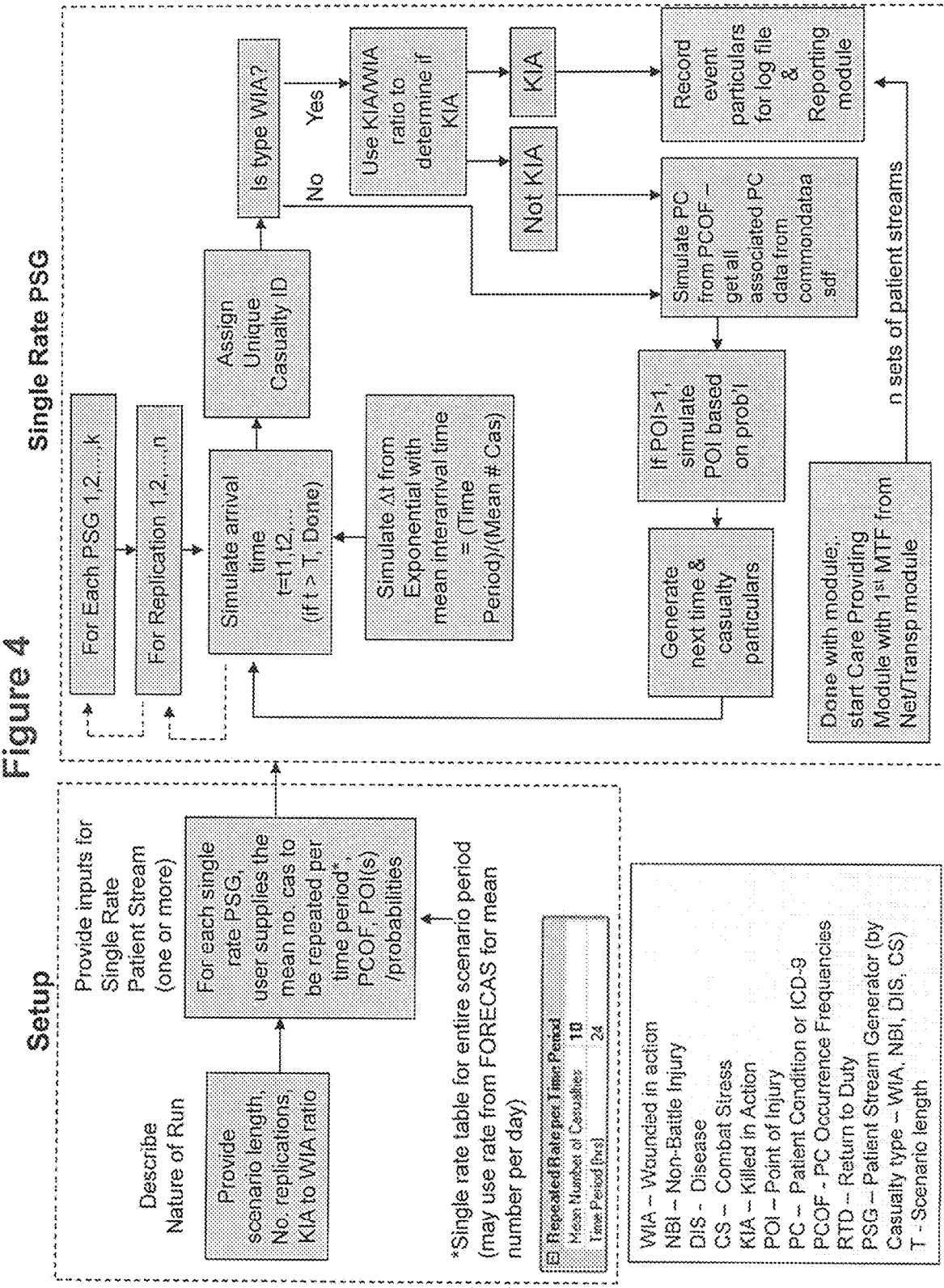

FIG. 4 is a diagram illustrating the data flow of a single rate PSG. The left of FIG. 4 shows the setup for the single rate patient stream generator (PSG). User provides inputs that describe the nature of a scenario simulation, such as scenario duration/length (T), number of PSG replications, and KIA/WIA ratio. User also provides specific inputs required for each single rate PSG, such as mean number of casualties per time block, PCOF, POIs/Probabilities. The casualty rate may also be imported from existing casualty generating software such as FORECAS. For each replication of a PSG run, a casualty arrival is stochastically simulated based exponential distribution with mean interarrival time=T/mean number of casualties, wherein T is Scenario duration/length. At any random time t, the program loops through for a new simulated arrival until time t is greater than T, the casualty generation simulation at that point is done. Each casualty created is then assigned a unique casualty ID. The casualty type is determined. If the casualty is not a KIA, a PC is random assigned to the casualty ID from PCOF. All associated PC data is randomly imported from database commondatta.sdf. If the casualty ID is determined to be a KIA, the event particulars are recorded in a log file, and stored in reporting module. In scenarios where there more than one POIs, the next POI is selected for casualty generation based on assigned probabilities. The casualty generation simulation is repeated until all replications is finished for each PSG, with n sets of Patient Streams created.

Figure 5:
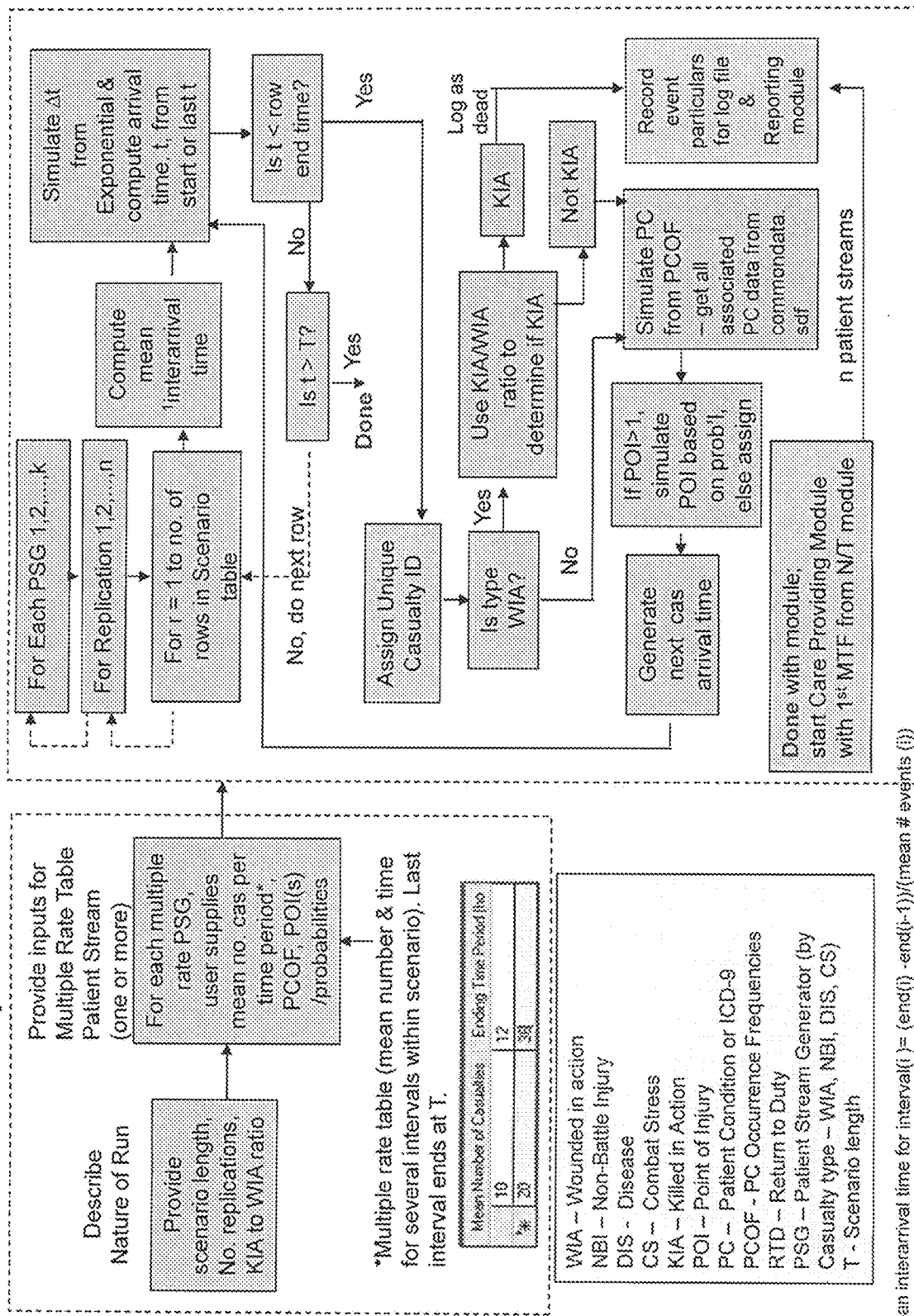

FIG. 5 is the flow diagram illustrating the data flow of a multiple rates PSG. As in FIG. 4, user setup is shown on the right of the figure. Each row of the multiple rate table contain mean number of casualties, and end time for a particular casualty generation interval within a scenario simulation. The basic decision flow diagram of multiple rates PSG is similar to that of a single rate PSG with a few additional steps within each replication designed to determine rate of a particular time interval. Starting from row 1 of the multiple rate table, a casualty arrival is stochastically simulated based on an exponential distribution with mean interarrival time=T/mean number of casualties, wherein T is Scenario length. At a random time t, if t is greater than row end time as listed in the multiple rate table, and greater than simulation duration T, the casualty generation run is done and a new replication is begun if necessary. If t is greater than the row end time but less than T, the stimulation run moves to the next row. If t is less than row end time the program loops through as in a single rate PSG.

FIG. 6 shows the flow diagram of a mass casualty event PSG. Similarly, setup of a mass casualty event simulation is listed on the left of the figure. MCEs' random interarrival time distribution follows the exponential distribution with random number of casualties per event determined via Geometric distribution. An example MCE table is shown on FIG. 6 on the left under title SETUP. Simulation Flow Diagram of MCE PSG is shown on the right of the FIG. 6, which is similar to multiple rate table PSG with only difference in simulation of number of casualties generated per event. After casualties are generated the simulation move to care providing module. Self/buddy aid (SBA) is assumed to occur immediately at POI.

Care Providing Module

The present invention allows simulation of patient flows within a MTF via the Care Providing Module. Different MTF may be selected in a simulation model, including self or buddy care at the point of injury, which is care provided by field-level corpsman or first responder; Battalion Aid Station (BAS) and; finally Shock Trauma Platoon (STP)/Forward Resuscitative Surgical System (FRSS), which can be a field hospital or a medical ship.

Figure 7:
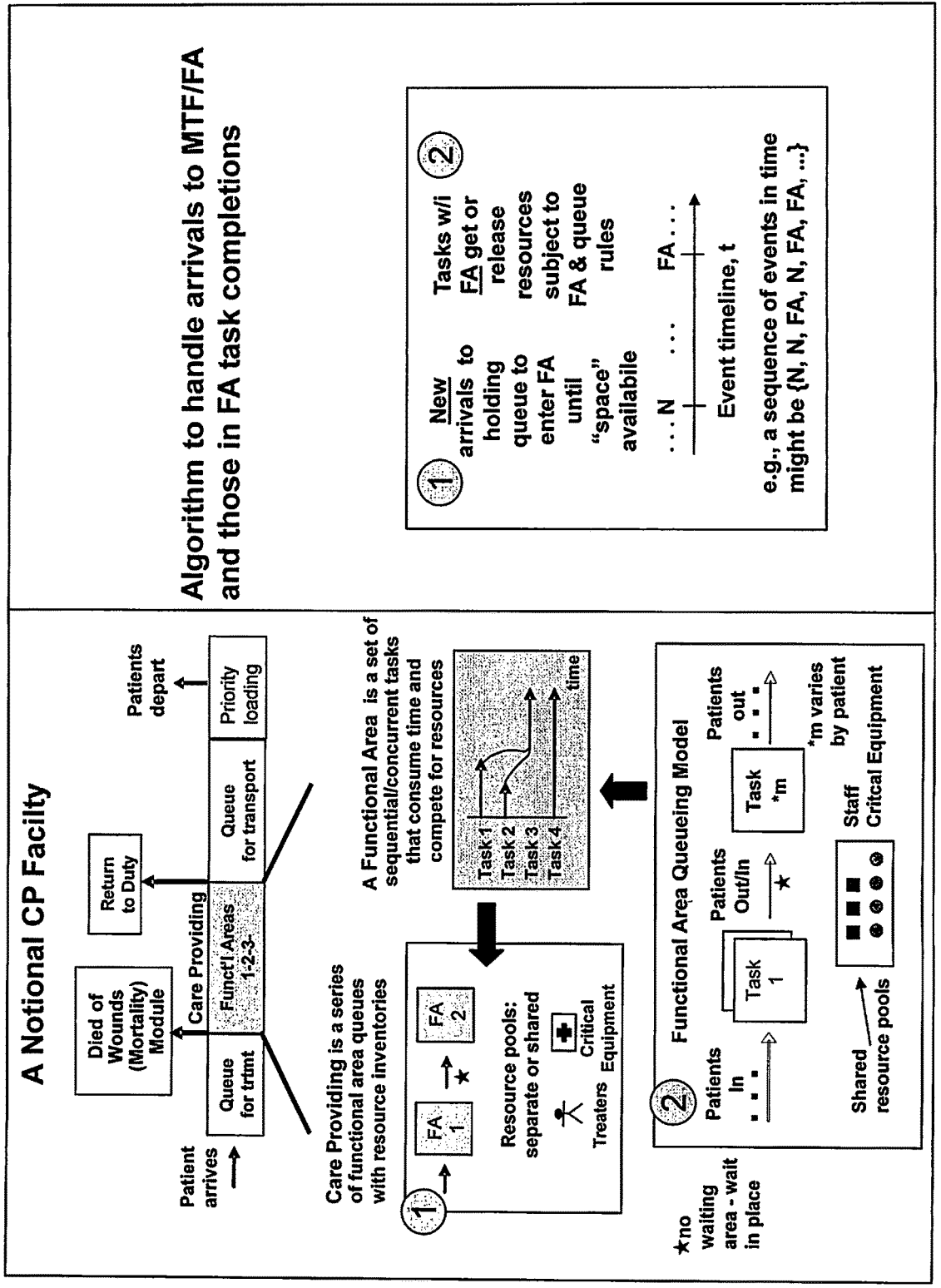

A notional care providing facility is shown in FIG. 7 (left) illustrating patient flow within the care providing module. As patient or casualty stream arrives at a care providing facility, patients died en route to this facility are identified and removed from the patient stream based on stochastic simulation of the Died-of-Wounds module, or may be based on the mortality rate of the previous MTF or duration transportation. Each casualty or patient is then queued for treatment, with its associated PC data is recorded. A queues allows various entities such as data, objects, persons, or events are stored and held to be processed later. In these contexts, the queue performs the function of a buffer. In this invention, patients are treated based on a service discipline such as first-in, first out (FIFO), or a priority scheme where the most severely injured patients are entered into service ahead of casualties with lesser injuries.

Each medical treatment facility of this invention is comprised of a series of functional areas with different medical capability and resource inventories, such as numbers of available medical spaces and critical equipment, and amount of consumable supplies. Within each functional area, a set of sequential or concurrent tasks may take place, which consume time and compete for resources. Examples of a functional area may be a medical image facility, a hospital bed or an operation room. Each casualty is assigned different tasks based on its PC. A task is a medical procedure performed on a patient. Examples of tasks supported by a functional area may include physical examination of the patient; a treatment/laboratory tests, such as suture a wound, blood draw, prepare a patient for operation, or performing X-ray; or an administrative task such as arrange for transportation. FIG. 7 (left Box #2) illustrates the general flow diagram of a functional area. A patient enters a functional area to have task 1 completed, consuming resources from the shared resource pool, and occupies the needed equipment for a period of time. Once task 1 is completed, the patient moved onto the next task need to be completed according to the patient condition associated with the patient/casualty with no wait time. Once all required tasks that are supported by this functional area are completed, the patient/casualty may a. be discharged and removed patient stream if all treatment tasks associated with a particular patient condition are completed; data associated with patient ID are recorded;

b. enter a second functional area within the same care providing facility if additional tasks need to be completed at this care providing facility according patient condition assigned to this patient/casualty ID; or c. advance to the network/transportation module to be moved to the next care providing facility supporting additional tasks associated that this patient/casualty ID according to the assigned patient condition.

Figure 8:
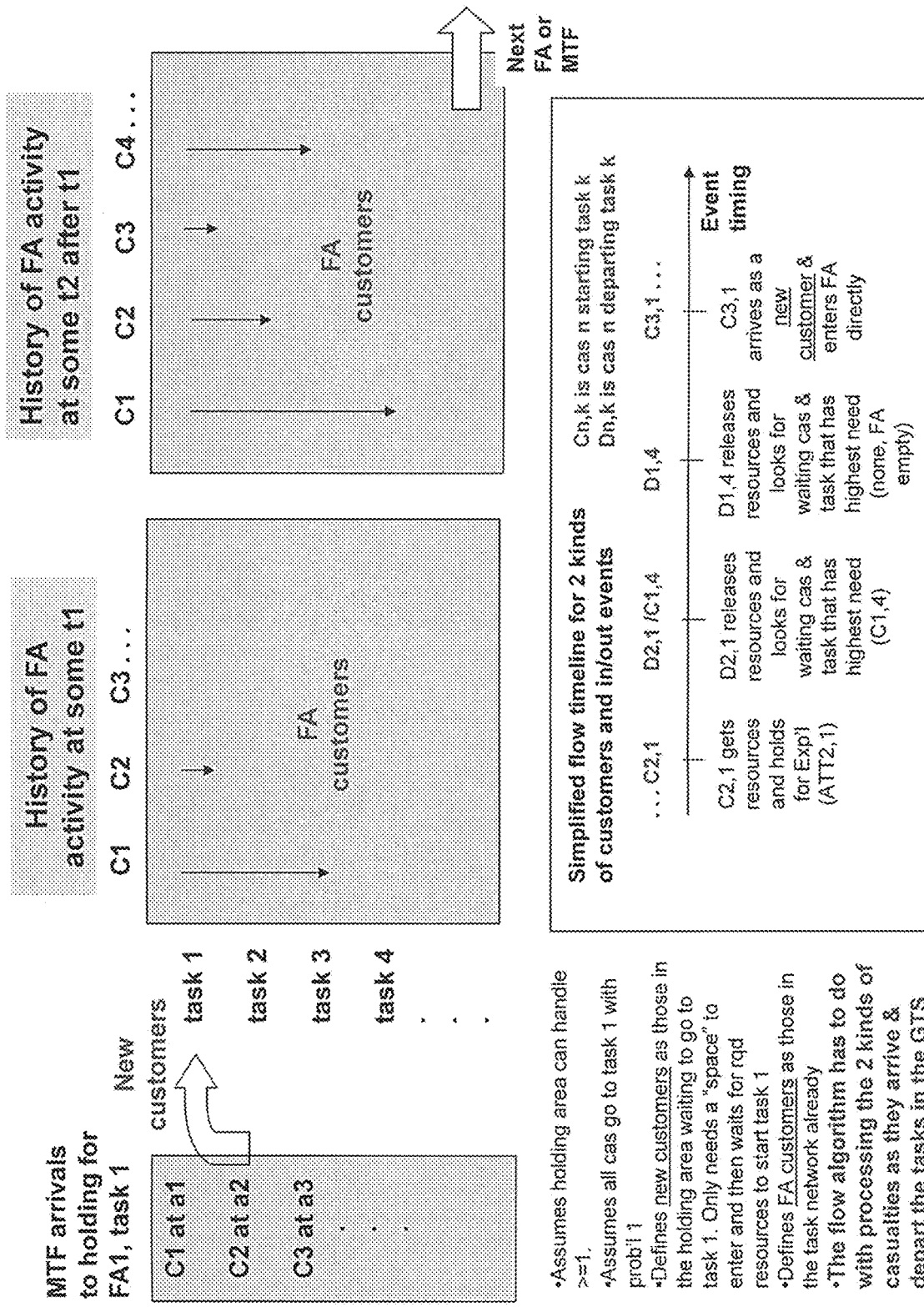
Figure 9:
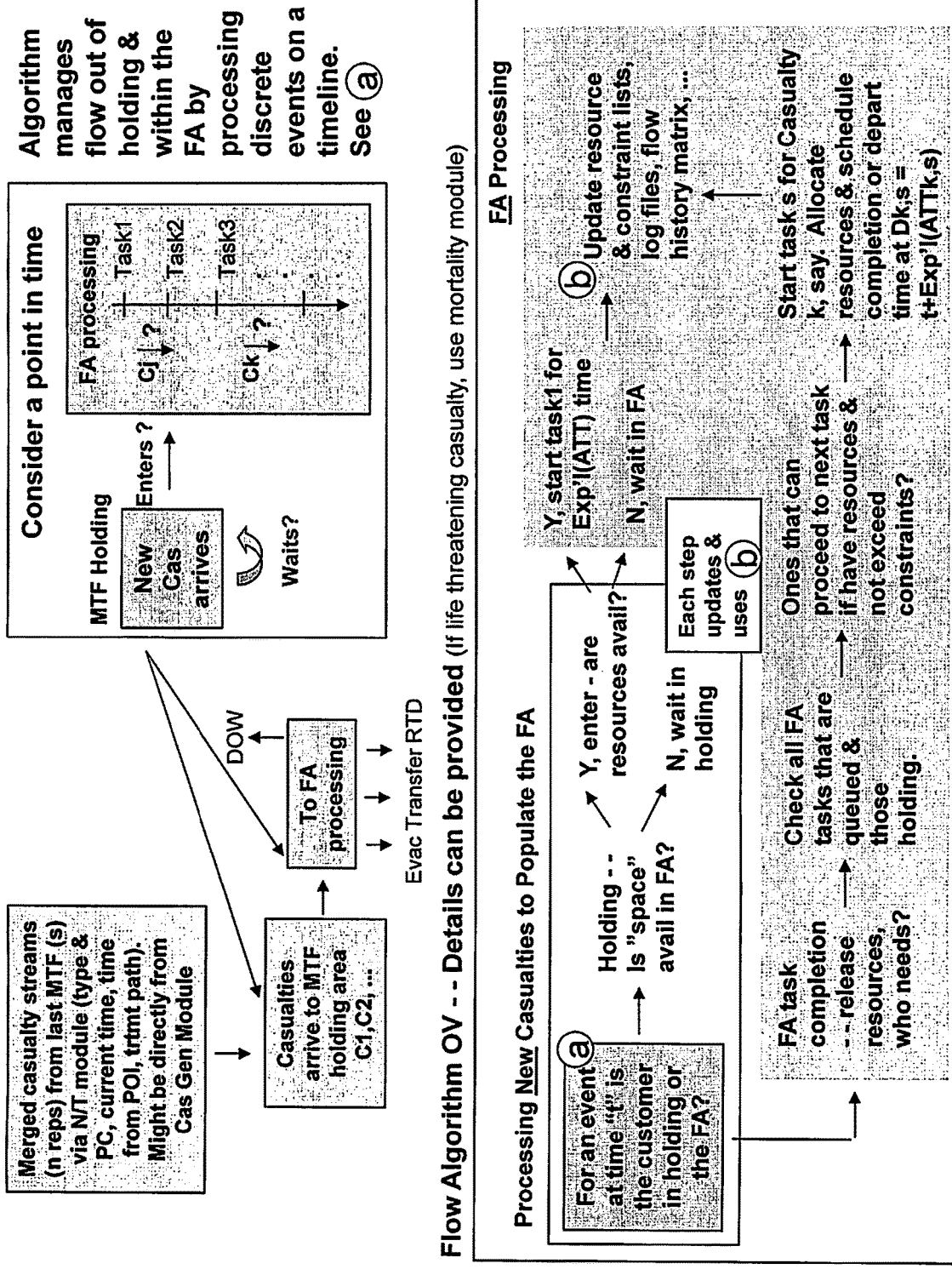
Figure 10:
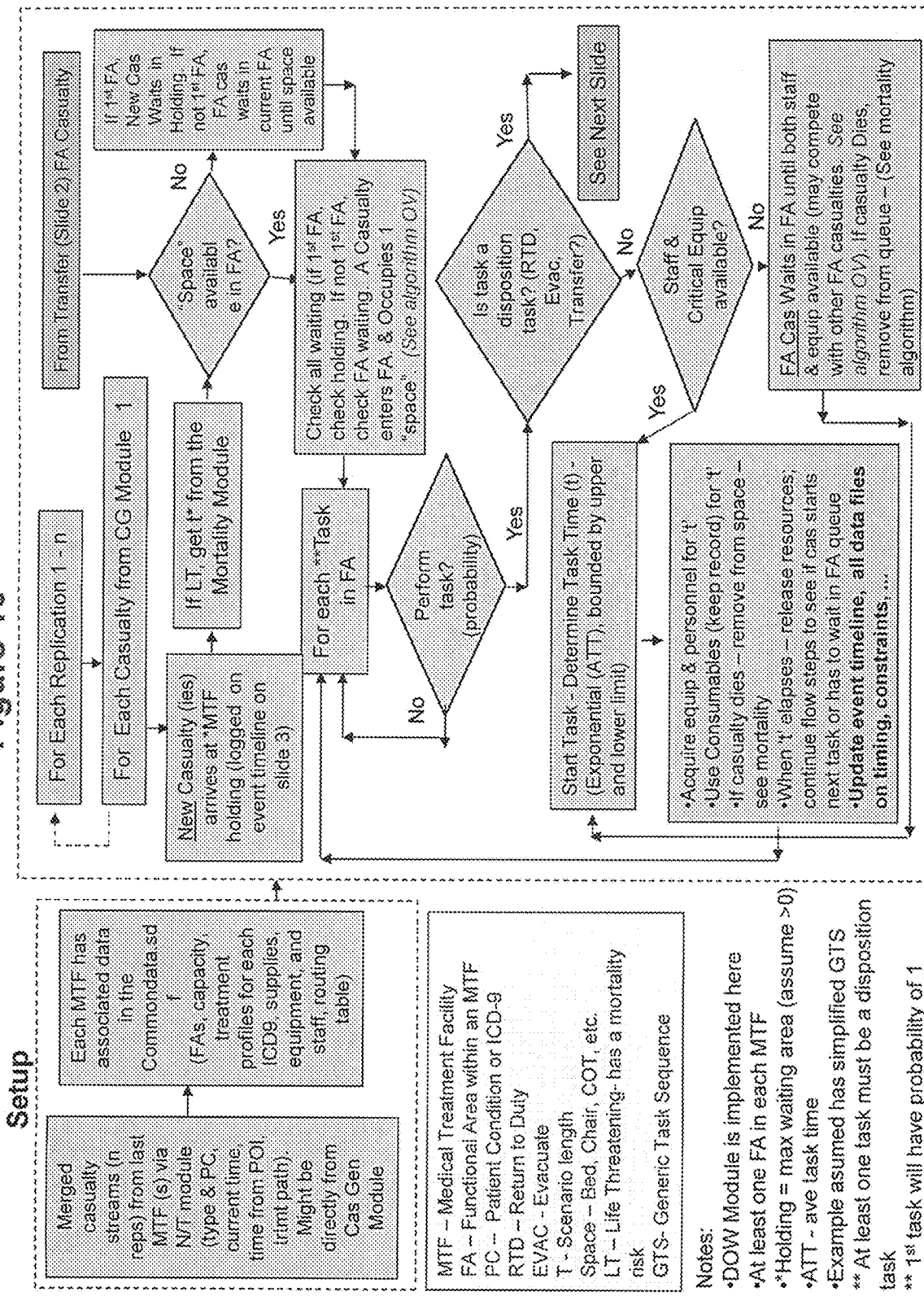

FIGS. 8-10 illustrate how Care Providing Module of this invention handles new arrival at a care providing facility (MTF)/functional area (FA) vs. existing casualties already held within a care providing facility (MTF)/functional area (FA) completing their tasks. As shown on FIG. 7 (right), at a random point in time, new arriving casualties reach a MTF try to enter Functional area 1 while a mix of casualties already waiting in Functional Area 1, trying to complete their tasks. Competition for staff and resources is subject to a multitude of restrictions and queue rules.

An example is shown in FIG. 8, casualties C1, C2, and C3 . . . arrive at a MTF at different time a1, a2, and a3 . . . etc. from a previous MTF via the transportation and network module. Each casualty is associated with patient specific data including but not limited to casualty type, patient condition, current time, the time from POI, treatment paths etc. Treatment path data are what treatments the casualty has received from POI. Each new customer (newly arrived casualty) upon arrival is put into a "holding area" waiting for to go to task 1. Each new patient may have a different first task in a FA, which is depending on the patient condition and probability of occurrence. Once a "space" opens up in a FA, the next new patient takes that space, and is treated as a FA patient This customer then waits for required resources to free up to complete his tasks 1. Casualty with the highest need will take priority over casualty and task with less urgent need. As a patient completes one task, it waits for its turn to complete the next task within the same FA or MTF. When that casualty completed all tasks within a FA or MTF, it moves to the next FA or MTF. The logic flow within a care providing module thus has to do with handling these two kinds of casualty as they arrive and depart the task in the generic test sequence. An exemplary flow timeline is shown in the right lower box of FIG. 8, demonstrating how care providing module handles the two types of patients. C n, k is casualty No. n starting task k, and D n, k is casualty No. n departing task k. On the far left side of the timeline casualty No. 2 gets first available resources, and holds them during the simulated time period for completing task 1. Casualty 2 releases resources when task 1 is completed, and the program looks for the next waiting casualty tasked with the highest need based on patient condition code. When more than one casualty is in a queue, the simulation looks at the treatment priority of the patient code (may be different for each FA) and the highest treatment priority is selected first. If all treatment priorities are the same, the next casualty ID for treatment is selected based on FIFO method. In this example, casualty No. 1 with task 4 is selected. Casualty 1 then holds on to the resources for task 4 during the simulated period of task 4. When casualty 1 completes task 4, the program looks at the awaiting casualty, and selected the casualty with the highest need. However, FA is empty at this point with no more awaiting casualty. Program waits until casualty 3 arrives at this FA as a new patient. Because FA is now empty and space is available casualty 3 enter the FA immediately and begins task 1.

FIG. 9 shows the algorithm overview of the sorting strategy used in the care providing module. When casualties arrive at a MTF, they are placed in a holding area, and are each assigned a patient number. They are then undergoing FA processing. Patient deemed MA using the DOW module, is removed from the patient stream and their data recorded in data access module. The other new casualties wait for the next available space in the FA to complete their assigned tasks. All patients enter the First FA of an MTF. The First FA is defined in the common data. The order of other Functional areas within a MTF is defined by the patient's task list. If a space becomes available in the FA, they will enter the FA. If resources for completing task 1 associated with this patient are available within the FA, this customer will proceed to complete task 1 and hold required resources for the simulated period of task 1 based on an average treatment time for task 1. If the required resource is not available, this casualty waits in the FA. Each time a task is completed, related resources is freed. The program will check all the casualty tasks within the FA, and those of the casualties in the holding area. If resources are available, and do not exceed constraints, the casualty proceeds to the next task.

Not all patients will visit all FAs within an MTF. The tasks that move patients from one FA to another are disposition tasks and vary for each patient. The task list for a patient code in an FA must contain at least one disposition tasks and the probability of the task occurrences must sum to 100%. For example, a patient's task list for FA Triage, may have a 50% probability of transferring to the OR and a 50% chance of transferring to the Ward, indicating that not all patients with this patient code will go to the FA OR.

Tasks within an FA have a sequence number. Tasks are performed in this order for each patient. Tasks that have identical sequence numbers are considered to be concurrent tasks and may be performed simultaneously given the resources are available. The ranking scheme for casualties only comes into play when casualties are queued. FAs may treat one or more casualties at one time (max casualties in FA), so multiple casualties may be treated at once.

The program updates resources, constraint lists, log files, and creates a history matrix including the completion/departure time for that casualty. For example, when Casualty k completes its task s, its departure time would be denoted by Dk, s=t+Exp'l (ATTk, s), wherein t is the starting time and ATTk,s is the average task time for completing task s. This task time is simulated from exponential distribution.

A more detailed logic diagram for the care providing module is illustrated in FIG. 10. To run a simulation using the care providing module, existing casualty must be merged with casualty streams from the network and transportation module or from the casualty generation module. Each casualty has associated PC data. Each MTF has associated data in the Commondata.sdf, containing information such as functional areas, capacity, and treatment profiles for each PC (codified using ICD9), supplies, equipment, staff, and MTF routing table etc. Several assumptions were made in the implementation of the care providing module, it is assumed that a. Holding area can handle at least one incoming casualty;
    b. All casualty got to task 1
    c. There-is at least one functional area in each MTF.

For each casualty stream from the casualty generation module or the network/transportation module, the new casualties are logged onto an event timeline as in FIG. 8. If the casualty's PC is categorized as Life threatening (LT), a life-time is simulated using the DOW module, and WIAs en route maybe removed from the casualty stream (see DOW module). The program then checks for space availability within a FA.

Figure 11:
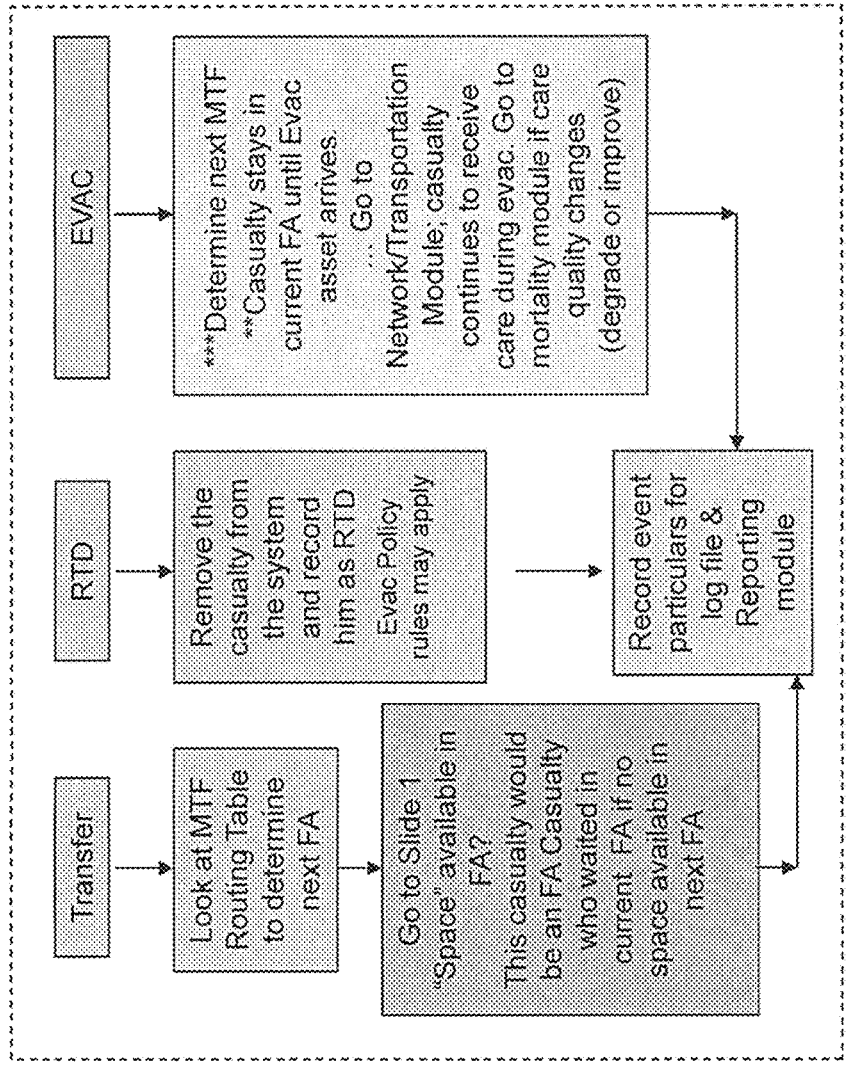

During a simulation, if a space becomes available, the program will check all casualties waiting for treatment. If this is the first FA, the program checks casualty list in holding to pick the next casualty to be serviced. If it is not the first FA, the program will check casualties waiting in other FAs of the same MTF. First FA for this MTF is the same for all patients who enter this MTF, which is defined in the Common Data. Once a casualty selected for the space, it enters the FA, and occupies the available space. When there is no space available in a FA, the newly arrived casualties will wait in holding, and casualties already entered the MTF, waits for treatment in their current FA. Each task in a FA has an associated probability for being performed. If a task is not to be performed, the program moves to the next task for FA. If a task is to be performed for a casualty, the program checks to see if the task is a disposition task, which include return to duty (RTD), evacuate (Evac), or transfer. If the task is not a deposition task, the program checks to see if staff and resources such as critical equipment required for this task is available. If they are available, the program will start the task for the simulated task time associated with the particular task. When simulated task time elapses, the resources and personnel became available for the next casualty. Used consumables are deducted. If a casualty died in FA according to the DOW module, it is removed from the patient stream, and the casualty's space is freed up. In cases where the task is a deposition task, the logic flow is illustrated in FIG. 11. Casualty maybe transferred to the next FA according to MTF routing table if space is available in the next FA. Otherwise, the casualty would be an FA casualty who waits in current FA until space became available in the next FA. For casualty being tasks for RTD, they are removed from the system and are recorded as RTD. Evacuation policy rules may apply. For casualty with EVAC task, determination will be made as to the next FA. Casualty stays in current FA until Evacuation assets arrive. Simulation will be handled by Network/Transportation Module. All event particulars for deposition tasks are recorded in the File & Reporting Module.

The Died-Of-Wounds Module

One of the challenges in crisis medical planning is estimating died-of-wounds due to a delay in treatment, or simply mortality estimate. Typical question of interest include:

i. How many lives can be saved if a forward surgery system is present near the combat area?
    ii. What is the best way to integrate, in time and space, transportation and Medical treatment facilities (MTF) assets to reduce casualty losses in a deployed network of care?
    iii. How do spikes in casualty occurrences impact operating room throughput and mortality for various staff and equipment configurations?

The Died-of-Wounds module of this invention is based on the assumption that a seriously wounded casualty's time to death is a random variable that has a probability density function (pdf) with parameters dependent on the casualty's injury extent, current MTF capability, and past treatment history/timing. In each operation model using this invention, simulated draws are made from the pdf throughout a scenario to interject mortality events. Currently, the Weibull distribution is selected to be used based on an analysis of expert opinion data obtained from a panel of eleven military medical doctors convened and empirical data collected during historical military operations. The parameters of the distribution may change based on different historical data and expert opinion. For example, probability density function of Died-of-Wounds module in a natural disease response model may have different property influenced difference in the casualty's injury and extent, MTF capability, and past treatment history/timing. More objective data-driven stochastic models can be constructed using similar method to be used in medical planning of crisis response or natural disaster response.

In order to accurately determine the parameters of the Died-of-Wounds probability distribution function, a panel of subject matter expert (SME) was convened. The injuries as classified by International Statistical Classification of Diseases and Related Health Problems version 9 (ICD-9) are designated as having either a high, medium, or low risk of mortality within the first hour after wounding, where the probability of dying is greater than ⅔, between ⅓ and ⅔, or less than ⅓, respectively. The panel was conducted in a Delphi-similar manner, where a presumed number of battlefield casualties with various PCs developed by the Defense Medical Standardization Board. Each casualty is presumed to receive one of medical interventions for an injury:

1. by self or a buddy at the point of injury
    2. by a field-level corpsman (first responder);
    3. by the Battalion Aid Station (BAS) MTF; and, finally;
    4. by a Shock Trauma Platoon (STP)/Forward Resuscitative Surgical System (FRSS).

For each PC and treatment assumption, the panel was asked to estimate the fraction of casualties that would be expected to survive after specified time epochs, such as 10 minutes, 30 minutes, 1 hour, 3 hours, etc., in the various interventions or MTFs. The rather impressive matching of these expert, yet qualitative opinion results with the Weibull distribution, which was judged adequate for an initial implementation of a stochastic representation. Similar curves for medium and low risks of mortality were obtained.

The NMC CTR is a data warehouse composed of data sets describing events that occur to individual casualties, from the POI through the medical chain of evacuation and on to long-term rehabilitative outcomes. CTR can assist medical planners, systems analysts, and logisticians in planning for the random occurrence of injury types in treatment and evacuation scenarios of interest. These data sets were used as empirical means to confirm or augment medical logistics modeling assumptions of this invention. In particular, NMC CTR records related to Operation Iraqi Freedom are used in a statistical analysis of the usefulness of the Weibull distribution in describing mortality.

Throughout, the random life time T is assumed to have a pdf f(t) and a probability of surviving past time t given by the survival function S(t)=Pr[T≥t].

The Probability density function is defined as $f(t) = (b/a) * [(t/a)^(b-1)] * \exp[-(t/a)^b]$, $a > 0$, $b > 0$, $t > 0$.

Survival distribution function is defined as $\Pr[T > t] = S(t) = \exp[-(t/a)^b]$ Cumulative distribution function is defined as $\Pr[T \leq t] = F(t) = 1 - \exp[-(t/a)^b]$ Mortality function is defined as $h(t) = (b/a) * (t/a)^(b-1)$ h(s) is integrated from s=0 to t. The exponential pdf is a special case of the Weibull pdf, where the shape parameter b is 1.0; its hazard rate is constant. The parameter a is called the scale parameter.

The survival function, S(t), and hazard function, h(t), each giving a different view or interpretation of the mortality process, will be estimated from data plots and analytical means. Basically, the lengths of life times via the survival function and the rate at which deaths occur [given by the hazard function] are different views of the same process. It is assumed that the patients entering the surgical MTFs are a random sample from the OIF severely injured population, and the injuries incurred are a random sample of the battlefield wounds likely from theater operations. It is further assumed that the majority of patients arrive at the surgical MTFs directly from first responder treatment after a nominal delay. The basic approach will be to characterize the pdf of T by exploiting various features of the Weibull distribution.

Given the almost perfect straight-line fit of the Weibull hazard function to the empirical hazard function and the nice MLE agreement, it is suggested that the Weibull distribution is an adequate fit of mortality events for this data set. For completeness, a chi-squared goodness-of-fit test is conducted for a life table representation of the data on death times and numbers at risk. A computed value of 3.63 was obtained, and when compared with the chi-squared tabular value of 5.99 with two degrees of freedom and an of 0.05, a null hypothesis for the Weibull distribution to describe these data could not be rejected.

Weibull distribution parameters are shown in table 1, where the risk category/treatment path code is shown in column 1, and Weibull parameters are shown in corresponding columns of the same row. The code is composed of a first digit (1, 2 or 3 for risk category) followed by pairs xx for treatment locations. The treatment locations are designated 15 for self/buddy aid, 02 for first Responder, 03 for the BAS, 04 for the FRSS, 05 for the Surgical Company and 18 for the SST/STP. Eg, in the table "115" is a low risk injury treated at the SBA location, "3150204" is a high risk patient who has been treated at the SBA, the first Responder and is currently at the FRSS.

TABLE 1

Weilbull Survival Function Parameters

| Code | a | b | c |
|---|---|---|---|
| 115 | 18.7 | 0.82 | 1 |
| 215 | 2.2 | 0.65 | 1 |
| 315 | 0.4 | 0.53 | 1 |
| 11502 | 22.6 | 0.98 | 1 |
| 21502 | 9.9 | 0.62 | 1 |
| 31502 | 2.2 | 0.67 | 1 |
| 1150203 | 92.8 | 0.57 | 1 |
| 1150204 | 99.5 | 1 | 1 |
| 1150218 | 543.4 | 0.5 | 1 |
| 2150203 | 26.1 | 0.6 | 1 |
| 2150204 | 49.5 | 1 | 1 |
| 2150218 | 501.7 | 0.44 | 1 |
| 3150203 | 7 | 0.57 | 1 |
| 3150204 | 32.8 | 1 | 1 |
| 3150218 | 396 | 0.42 | 1 |
| 115020304 | 99.5 | 1 | 1 |
| 115020305 | 99.5 | 1 | 1 |
| 115020318 | 99.5 | 1 | 1 |
| 215020304 | 7.8 | 1 | 1 |
| 215020305 | 7.8 | 1 | 1 |
| 215020318 | 7.8 | 1 | 1 |
| 315020304 | 5.7 | 1 | 1 |
| 315020305 | 5.7 | 1 | 1 |
| 315020318 | 5.7 | 1 | 1 |

Note:
Parameters {a, b, c} used in Weibull survival function $S(t) = C \times \exp^{-(t/a)^b}$, wherein 1 = low risk, 2 = meditun risk and 3 = high risk FIG. 12 shows a top-level view of the algorithm of the Died-of-Wounds module (in the figure θ equals the elapsed time B-A).

A death time, t*, through MTF' & ERC' is simulated at time point A (by inverting F(t) with Weibull coefficients {a,b} conditional on patient condition, path history and MTF'). If t*≤B-A=θ, then the casualty dies at t* and is removed from the simulation. All medical resources are freed up (during a task or in queueing for a task waiting to be started). If t*>θ, then the casualty survives this MTF' and ERC', and starts over with a new t* from an improved F(t) in the next facility, MTF", which is an assumed growth in survivability model.

Figure 13:
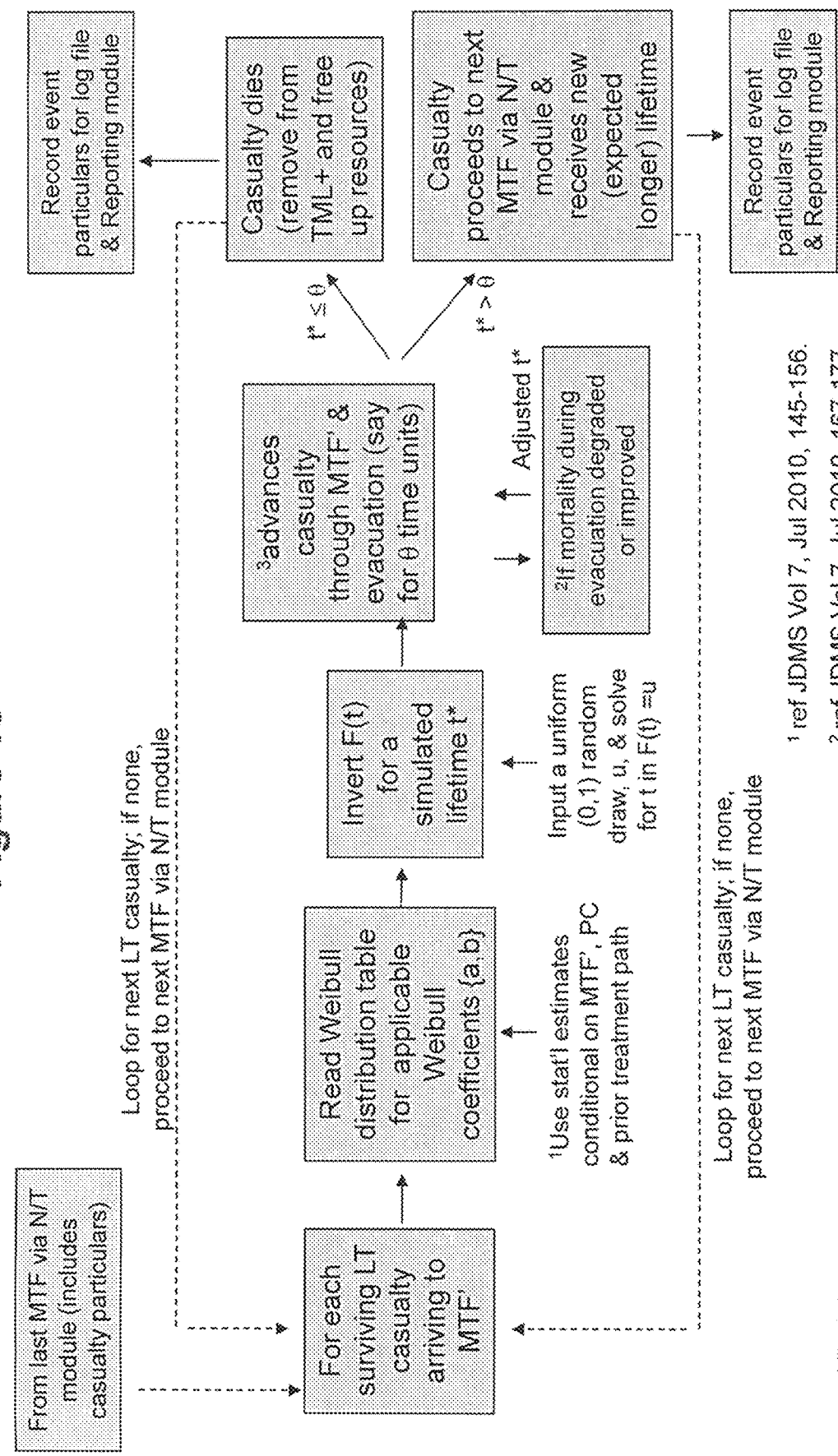
FIG. 13 Shows the Flow Chart for the Mortality (or Died-of-Wounds) Module

A more detailed example flow diagram for the Died-of-Wound module is shown in FIG. 13. When each surviving LT casualty arrives (casualty particulars are associated) at MTF via N/T module, the program reads the Weibull distribution table for coefficient a, b and c, which is on conditional on MTF', PC & prior treatment path. Invert F(t) for a simulated lifetime t*. Advances casualty through MTF' & evacuation (say for θ time units), if θ is greater than t* casualty proceeds to the next MTF via N/T module & receives new lifetime. If θ is less than or equal to t*, Casualty dies, it is removed from casualty stream, resources are freed. Event particulars are recorded for the file & Reporting module.

The Network and Transportation Module

Figure 14:
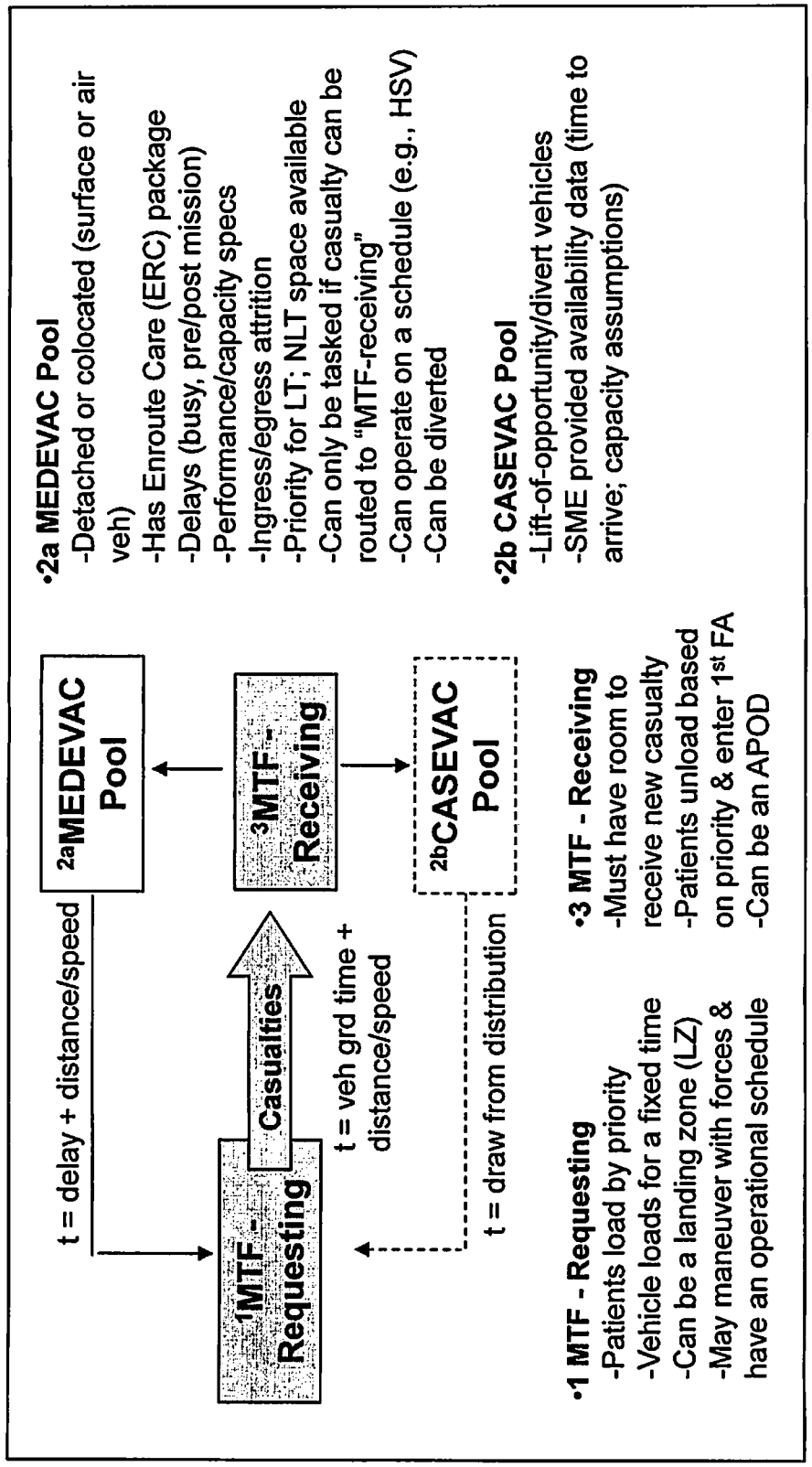
FIG. 14 is a diagram showing an embodiment of the data access module.

An overview of the routing & transportation module is shown in FIG. 14, which includes three general components: requesting MTF, vehicle Pool, and receiving MTF. An example network and transportation network is shown in FIG. 2. An MTF's location is defined by the user according to the medical logistic plan. An MTF may maneuver with the force, and may have an operational schedule. An operational schedule is a timing plan for when the MTF is open to receive patients and when it is down due to a maneuver operation to change locations. MTFs are connected by routes to direct patient flow. Each route has a user-defined distance, possible schedule, priority and is either a walking route or non-walking route. Priority is used to determine which MTF is first considered if there are multiple MTFs available. When transport is required, casualties are loaded using a fixed time according to the transportation type. A vehicle pool is comprised of a collection of transportation assets. The transportation assets may be detached or collocated and may be a surface or air vehicle. Transportation types are included in the commondata.sdf, and is each defined by speed, capacities, ranges, ground wait time, pre/post mission delays and ambulance/litter load/unload time. Each vehicle has a predefined Enroute care (EDC) package identifying the resources and staff available to the patient during transport. The user may assign one or more transportation types to each route and may assign a schedule for the transportation assets and set priority to reflect the desired concept of operations for a particular scenario. As transportation assets are added to a transport pool, they have a default priority of "1". When all transports have the same priority, the transport that can with the fastest travel time is selected. If the user sets the priorities, then the highest priority is selected first and so forth. Transportation is unavailable during post-mission delay, and there may be user-defined downtime due to maintenance including the loss of a vehicle. User may provide the probability of down time or lost of a vehicle. Casualty is loaded for transport based on priority. Priority is given to life threatening casualty over non-life threatening casualty. The availability data for each type of transportation assets such as capacity assumption are determined by subject matter expert. A receiving MTF must have room to receive a new casualty before transportation can be tasked. User also has the option of defining routing policies for an MTF, which defines the routes that specified casualties are allowed to travel on. Patients are unloaded based on priority. Unless otherwise defined by the user, it is assumed that casualties receive the same level of care as the last MTF during transport. However, the user may also adjust the mortality risk associated with the transport as probability. Life threatening casualties may die while waiting for transport or while enroute, which is simulated using DOW module.

Figure 15:
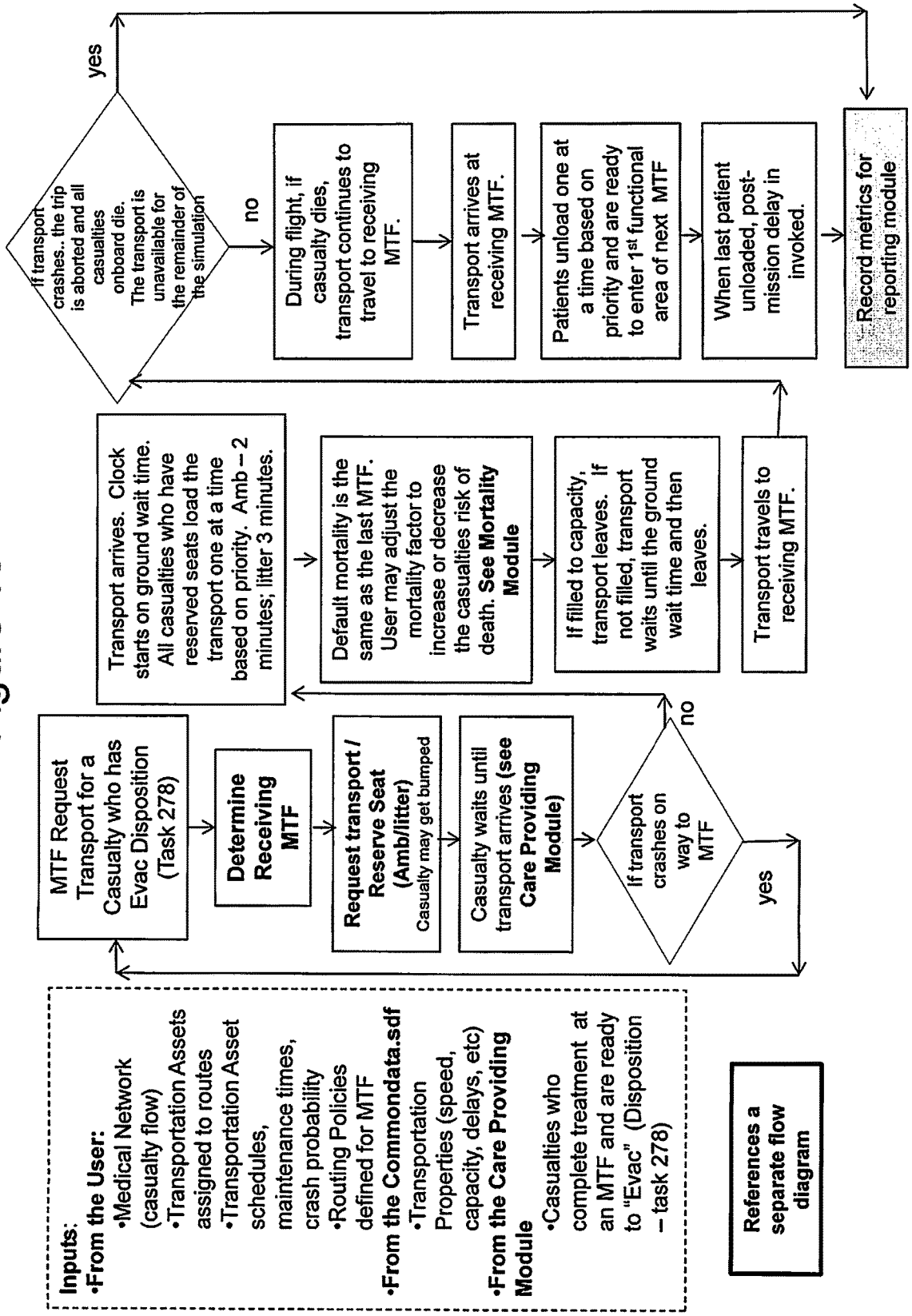
FIG. 15 is a detailed logic flow of the network and transportation module

FIG. 15 shows the overall Network/Transportation Module logic diagram. Before a simulation, user must set the medical network, transportation assets, maintenance time, crash probability and assign routes, and provide transportation schedule and routing policies for the requesting/receiving MTFs. Requesting MTFs are assigned routing policies and possible outgoing routes. Transportation assets are assigned to the receiving MTF. Transportation assets are assigned maintenance times, crash probabilities, schedules. The additional information is imported from commondata.sdf. Information relating to casualties who are ready to be evacuated is imported from the Care Providing Module (see Evac. FIG. 11)

A simulation using the network/transportation module begins with a MTF requesting transport for a casualty who is tasks for Evac Disposition. A receiving MTF is then determined based on routing policy. A reservation is made for a seat on a transport asset. The type of transportation depend on the route available for that casualty, and transportation assets available for that route. A casualty then waits until transport arrives. The casualty may get bumped by a casualty with higher priority during waiting time. A new request must be made if the transportation asset crashes on the way to requesting MTF. When transport arrives, clock starts running on ground waiting time. Ground waiting time is the maximum time a transport will WAIT for casualties to get ready to load. If set to "0", all casualties ready to be loaded will be loaded, then the transport leaves . . . does not wait for more. If set to 15 minutes, the transport will load all that can be loaded within 15 minutes and leave. All casualties who have reserved a seat on this transport will be loaded one at a time according to priority and loading time. The default mortality rate is the same as the last MTF. If user adjusted the mortality rate for the transport, the casualty risk of death will increase or decrease accordingly. When reaches its capacity, the transport vehicle will leave. If transport is not filled to capacity, transport will wait until the ground wait time runs out and then leave. The Network and Transportation Module also allows introduction of transport crashes into the simulation. The probability of crash rate is set by the user before running the simulation. If transport crashes, the trip is aborted and all casualties onboard die. The patient's data recorded. The transport vehicle will become unavailable for the remainder of the simulation. Other transport travel to the receiving MTF. If during the transport a casualty dies, transport will continue to travel to receiving MTF. Upon arrival at the receiving MTF, patients are then unloaded one at a time based on priority according to unloading time. The patient is then ready to enter the first FA of the receiving MTF. As mentioned in the care providing module, if there is no space available in the first FA of the receiving MTF, the patient waits in holding area. When last patient is unloaded, post-mission delay is invoked and the vehicle is unavailable for transport during this delay. Metrics related to the transportation is recorded in the recording module.

Figure 16:
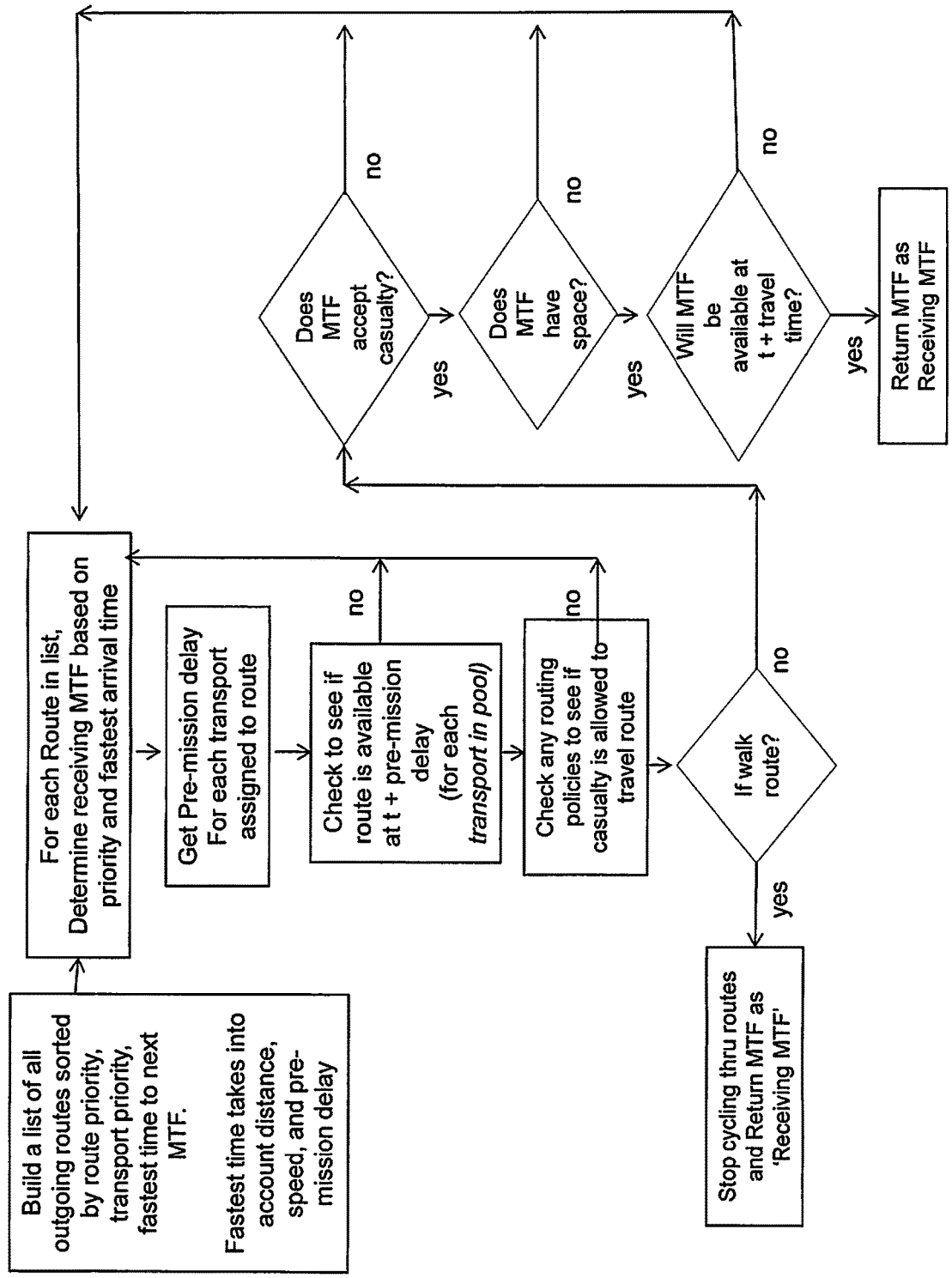
FIG. 16 is a detailed logic diagram illustrating the determination of the receiving MTF

FIG. 16, shows how a receiving MTF is determined. A list of all outgoing routes is first sorted by route priority, transport priority and/or fastest time to next MTF. The fastest time takes into account of distances between the MTF, speed of the transport vehicle, and pre-mission delay. For each route on the list, the program then determines receiving MTF based on priority and fastest arrival time. First, each transport that is assigned to a route is checked for availability at the t+pre-mission delay, wherein t is the time of inquiry. If no transport is available, the program loops back to check the next route on the list. If a transport is available, the program checks routing policies to see if casualty is permitted to travel by this route and transport. If the transport and route is not allowed via routing policy, the program loops back to the next route on the list. If the transport is allowed, and is a walk route, the program stops cycling, and returns the MTF as the receiving MTF. If the transport is allowed, and is not a walk route, the program checks to see 1) if the MTF accepts casualty? 2) does the MTF have space? 3) will the MTF be available at t+travel time? If the answer to these three questions is "yes", the MTF is returned as the receiving MTF, otherwise, the program loops back to check the next route on the list.

Figure 17:
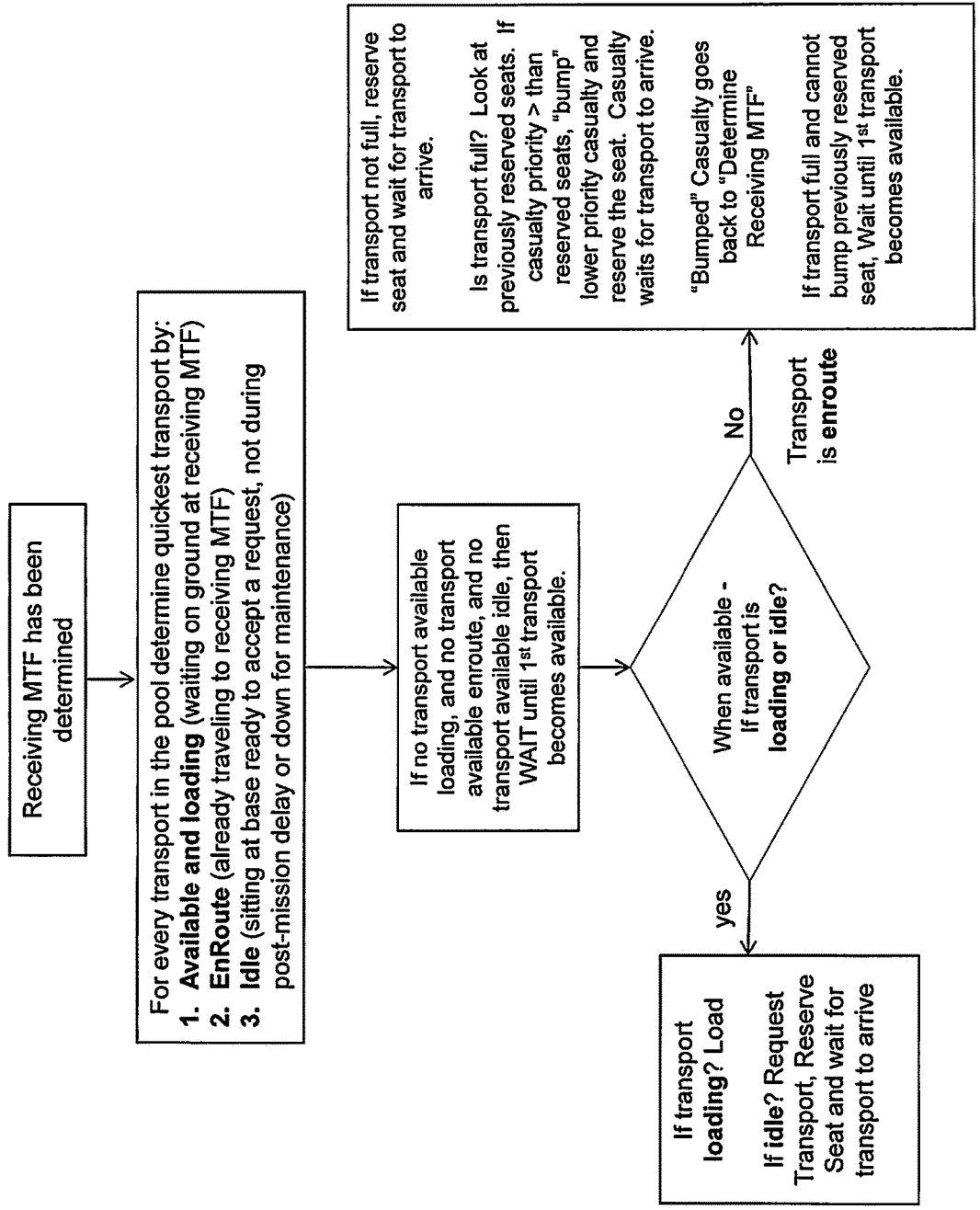
FIG. 17 is a detailed logic illustrating the process of requesting/reserving a transport.

FIG. 17 shows the general logic flow of requesting a transport. Once a receiving MTF has been determined according to the process of FIG. 16, for every transport in the pool, the quickest transport is determined by asking three questions is 1) is there a transport available for loading at the pickup MTF? 2) is there a transport already traveling to pickup MTF and 3) is there a transport sitting idle at the receiving MTF ready to accept a request. The transport vehicle is deemed idle if it is not down for maintenance or in post-mission delay. If no transport is available under these three categories, the patients wait until first transport becomes available. When a transport is available for loading, patient will be loaded. If the transport is in idle condition, a request is made to reserve seat on that transport and patient wait for transport to arrive. If the transport is en route, the program checks the list of reserved seats for that transport. If the transport is not full, a seat on the transport is reserved and patient waits for transport to arrive. If the transport is fully reserved, casualties on the reserved list are checked for priority. A new patient with higher priority may bump a patient with lower priority off the reserved list. The new casualty will wait for transport. If the transport en route is fully reserved, and no patient can be bumped off the reserved list, the patient waits for the next available transport.

The Report Generation Module

Figure 18:
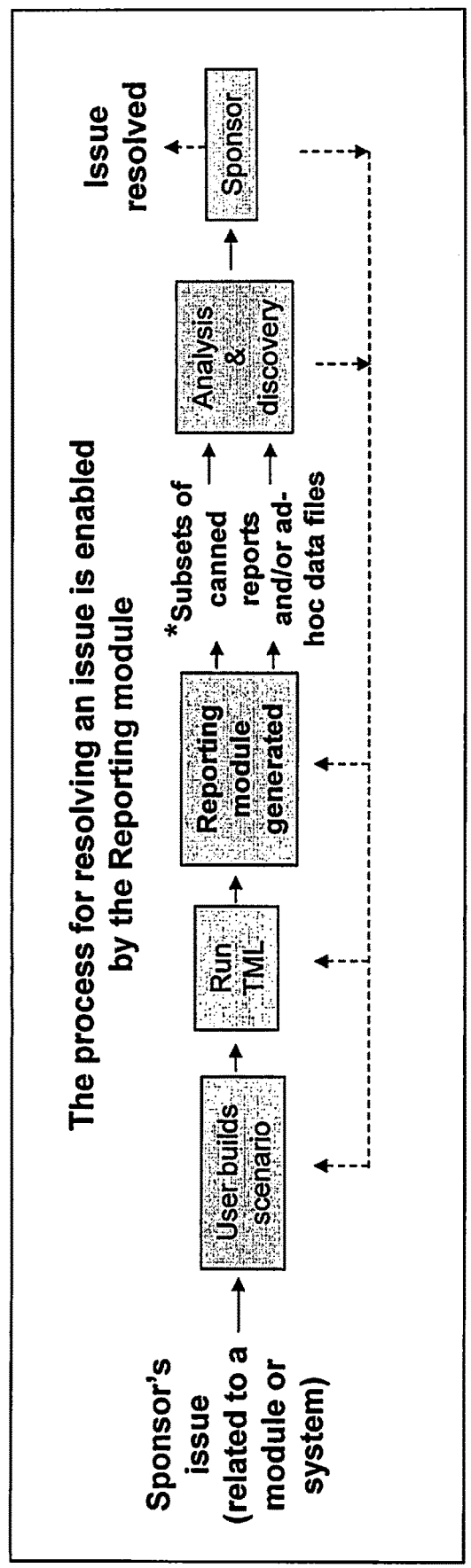
FIG. 18 is an overview of the reporting module.

FIG. 18 is an overview of the reporting module. The reporting module allows for approximately 45 canned charts, figures and tables; and virtually an unlimited number of ad-hoc reports provide the basis for resolving a sponsor's issue. Examples of the canned charts, figures and tables include but not limited to casualty arrival plots by time, statistics on types of injuries to include deaths and MTF throughput and resource utilization. The ad hoc reports can be designed by the user based on the need of the user. For example, a user may select one MTF or All MTFs for the report. A report may show the cumulative total of the demands on transportation by time, or the highest demand for transportation. This information allows the medical planner to get the maximum information about their logistic plan for a particular scenario.

The Access to Database Module

Figure 19:
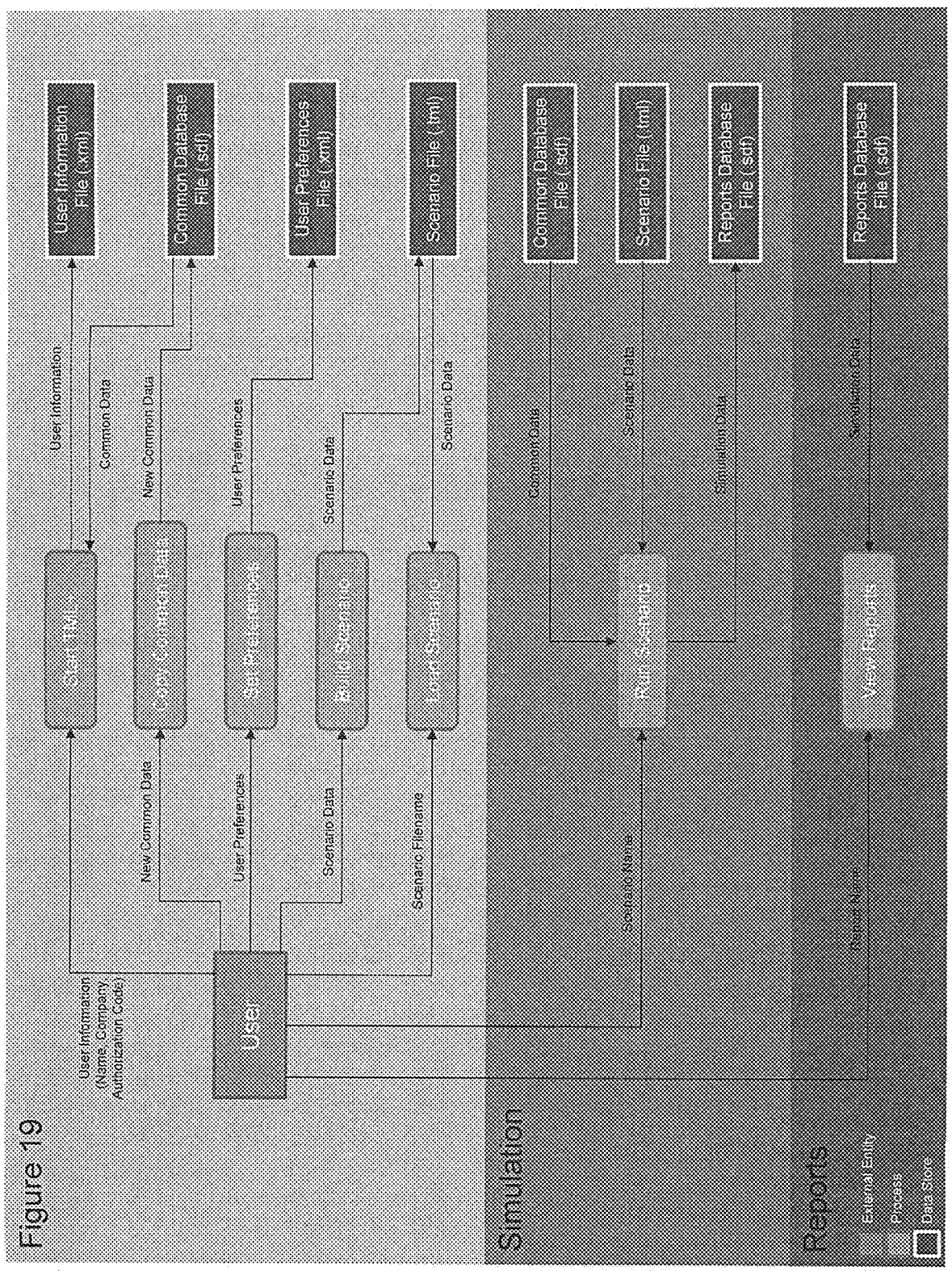
FIG. 19 is a flow chart showing data access module.

Multiple databases provide the information required for the simulation (FIG. 19). Before each simulation, the user first loads common data from data based called common database file. This file contains historical information collected or imported from other database with definite scenarios. Next, the user set preferences for the simulation, which are recorded in executable user preferences file. The user then builds a scenario for simulation according to the medical logic plan and scenario specifics. Scenario specifics are stored in scenario files and loaded before simulation. During a run of simulation based on the created scenario, information from common data and scenario data are used, while simulation data are recorded in report database files. A report with desired information may be customized and created by the user by accessing the information contained in the report database files.

The present invention is different from current planning tools (i) Open architecture, user-friendly graphical user interface;

(ii) Allows explicit representation of medical planning factors such as evacuation policy, evacuation delay, and skip;

(iii) Capability to model casualty mortality as a function of time before treatment;

(iv) Capability to model WMD/CBRNE exposure and treatment;

(v) Ability to model requirements by patient occurrences or patient admissions (vi) Ability to Calculate medical personnel requirements in Requirements Estimation and Course of Action Analysis mode;

(vii) Ability to control all business rules;

(viii) Capability to model Operating Room and Intensive Care Unit capabilities;

(ix) Capability to model Emergency Room, Triage, Lab, and X-ray without treating them as bed requirements;

(x) Ability to determine maximum medical workload given a set of capabilities;

(xi) Ability to determine best allocation of capabilities to meet all patient demands;

(xii) Supports analysis of casualty mortality relative to time and space on the battlefield and the capabilities of medical and evacuation assets;

(xiii) Capability to determine number and type of patients that occur between source facilities;

(xiv) Ability to move patients as they occur or to wait until transportation evacuation asset is full;

(xv) Ability to demonstrate greater detail moving patients on nonfixed wing assets;

(xvi) Ability to configure any transportation assets;

(xvii) Ability to visualize types of patient conditions (PCs) moved along routes to determine medical crew and enroute care requirements;

(xviii) Ability to implicitly route patients through system based on evacuation and skip policies;

(xix) Greater fidelity on modeling medical supply (CLASS VIIIA/B) requirements;

(xx) User definable patient arrival distributions at varying levels of user ability;

(xxi) Ability to model multiple runs and compare/contrast results.

If engineered carefully and analyzed properly, the present invention can also be used to build simulation models, which provide high-fidelity abstractions of real-world systems that are useful, relatively comparable to real-system output. However, for the forward-deployed planner reacting to a crisis, a simulation model is not an appropriate planning tool. Simulations require time to run experiments, analyze output data, and carefully reach meaningful conclusions about results. In a crisis situation, a planner might have only six hours between the time of alert and the beginning of plan execution. A simpler crisis-analysis planning (CAP) module is build to supplement the inventive planning tool. The CAP module approximates the stochastic processes in the present invention in an expected value sense, so a planner responding to a crisis can quickly discriminate between alternate courses of action (COAs) with reasonable quantitative justification. The CAP tool, built on the extensive data and research already behind this invention, enables a deployed medical planner to discriminate quickly, easily, and quantitatively between alternate medical COAs. The CAP uses analytical approximations or response surface methodologies, and experimental design concepts on simulation output of this invention to discriminate between reasonably different COAs.

The Development of this invention began in 2000. Since 2004, some 22 studies and analysis efforts within 14 Department of Defense organizations have been completed, which resulted in many improvements and modifications, as shown in different versions of the software. The following lists evaluation and validations of the software. The latest validation efforts occurred in 2012.

Example 1: The General Planning Process Using this Invention

Steps of the general planning process using this invention is listed below:

1. Start the TML+application.
2. Select a defined scenario or create a new scenario.
3. Build your scenario laydown.
  a. Enter the time period of your scenario in hours or days.
  b. Create a stream (or streams) of casualties.
  c. Create a medical network by dragging and dropping existing medical capabilities.
  d. Create evacuation routes by drawing routes between MTFs. Note that if the Map View is enabled, the route's distance is automatically computed.
e. Add transportation assets by dragging and dropping existing transportation types onto the MTFs.
4. Execute the scenario.
5. View various output reports on casualty generation, care providing, and transportation.

To conduct sensitivity analysis, the following additional steps are required:
1. Change a parameter.
2. Execute the scenario.
3. View various output reports on casualty generation, care providing, and transportation.
4. Compare the two runs.

Examples of user interfaces used by this invention is illustrated in Chapter 4 of the user's manual for Tactical Medical Logistics Planning Tool (version 4.1, Mar. 9, 2006), which is enclosed in the appendix of this application and is hereby incorporated by reference. Chapters 5 and 6 of the user's manual for Tactical Medical Logistics Planning Tool (version 4.1, Mar. 9, 2006) shows parameters may be changed in order to build and executing a simulation using this invention, which is enclosed in the appendix of this application and is hereby incorporated by reference. Examples of objects or reusable components that may be used to build an operational scenario are illustrated in chapter 9 of the user's manual for Tactical Medical Logistics Planning Tool (version 4.1, Mar. 9, 2006), which is enclosed in the appendix of this application and is herein incorporated by reference.

What is claimed is:

1. A method for conducting field medical services planning for an operational scenario, comprising:
   a) defining parameters of an planned operational scenario for evaluation;
   b) creating a medical logistic plan for said operational scenario by setting a plurality of parameters of said medical logistic plan, including
      i) providing a geographical view of said operational scenario and medical logistic plan including terrain;
      ii) setting up Medical Treatment Facilities (MTFs) for said operational scenario, comprising
         1. determining the locations of said MTFs; and
         2. defining each said MTF's capability and supply inventory, and
      iii) defining transportation parameters, comprising a crash probability, an assign routes, and a transportation schedule and routing policy;
   c) performing a simulation of said operational scenario using said parameters of said medical logistic plan;
   d) storing simulated data and said parameters of said operational scenario stimulation;
   e) repeating step (b)-(d) by changing said plurality of parameters of said medical logistic plan;
   f) reporting results of each of said simulation to a user including i) a casualty summary comprising casualty arrival plots by time; types of injuries, including deaths; ii) MTF and resource utilization; iii) cumulative total of the demands on transportation by time, or the highest demand for transportation; and
   g) selecting the most suitable medical logistic plan based on results of each said simulation;
   h) generating a list of medical capability and transportation assets needed for said most suitable medical logistic plan based on said casualty summary and the parameters of said medical logistic plan, wherein said list include:
      i) the quantity of supply, personnel, and transportation assets; and
      ii) locations of treatment facilities.

2. The method of claim 1, wherein step (a) further comprising
   a) selecting the type of said operational scenario;
   b) setting geographic location of said operational scenario; and
   c) defining the duration of said operational scenario.

3. The method of claim 1, wherein step (b) further comprising:
   a) identifying location of one or more point of injures (POI);
   b) setting locations and parameters of one or more medical treatment facility (MTF);
   c) defining service discipline; and
   d) defining parameters of one or more casualty generation events.

4. The method of claim 3, wherein step (b) further comprising:
   a) selecting a location for each of said MTF; and
   b) defining the type and parameters of each of said MTF.

5. The method of claim 4, wherein said type of MTF comprising:
   a) Self/buddy Aid (SBA);
   b) First responder;
   c) battalion aid station (BAS); or
   d) shock trauma platoon (STP)/Forward Resuscitative Surgical System (FRSS).

6. The method of claim 1, wherein results of said simulation comprising:
   a) patient disposition;
   b) casualty flow;
   c) casualty accumulation;
   d) consumable quantities;
   e) transportation usage;
   f) personnel utilization;
   g) equipment utilization; or
   h) a combined thereof.

7. A system for medical logistic planning of an operational scenario, comprising
   a) an implementable computer program designed to perform virtual simulation of an operational scenario based on a medical logistic plan;
   b) one or more computer database accessible to said computer program;
   c) a computing device controlling said computer program and said database; and
   d) an interface allowing a user to
      i) define parameters of said operational scenario including
         a) MTF parameters, comprising MTFs' capabilities, locations, and inventory; and
         transportation parameters, comprising a crash probability, an assign routes, and a transportation schedule and routing policy and medical logistic plan
      ii) generating a report on a simulation, including
         a) the quantity of supply, personnel, and transportation assets;
         b) casualty arrival plots by time;
         c) types of injuries, including deaths;
         d) MTF and resource utilization;
         e) cumulative total of the demands on transportation by time, or the highest demand for transportation; and
         f) locations of treatment facilities.

* * * * *